(12) United States Patent
Fischer et al.

(10) Patent No.: US 7,961,318 B2
(45) Date of Patent: Jun. 14, 2011

(54) CIRCULAR BIREFRINGENCE REFRACTOMETER: METHOD AND APPARATUS FOR MEASURING OPTICAL ACTIVITY

(75) Inventors: Peer Fischer, Belmont, MA (US); Ambarish Ghosh, Norwood, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 236 days.

(21) Appl. No.: 12/305,840

(22) PCT Filed: Jun. 27, 2007

(86) PCT No.: PCT/US2007/072248
§ 371 (c)(1),
(2), (4) Date: Dec. 19, 2008

(87) PCT Pub. No.: WO2008/002981
PCT Pub. Date: Jan. 3, 2008

(65) Prior Publication Data
US 2010/0231911 A1 Sep. 16, 2010

Related U.S. Application Data

(60) Provisional application No. 60/806,074, filed on Jun. 28, 2006.

(51) Int. Cl.
*G01J 4/00* (2006.01)
(52) U.S. Cl. .................................................. 356/364
(58) Field of Classification Search .................. 356/364
See application file for complete search history.

(56) References Cited

U.S. PATENT DOCUMENTS

| | | | |
|---|---|---|---|
| 5,486,940 A * | 1/1996 | Fergason et al. | 349/122 |
| 6,166,807 A | 12/2000 | Kawamura | |
| 6,466,320 B1 | 10/2002 | Kawamura | |
| 6,620,622 B1 | 9/2003 | Kawamura | |
| 6,687,012 B2 * | 2/2004 | Sanzari | 356/484 |
| 7,301,633 B2 | 11/2007 | Gibbs et al. | |
| 7,599,062 B2 * | 10/2009 | Smith | 356/367 |
| 2003/0081221 A1 * | 5/2003 | Sanzari | 356/484 |
| 2005/0094144 A1 * | 5/2005 | Gibbs et al. | 356/365 |

OTHER PUBLICATIONS

Cartwright, Jon; "Chiral Liquid Splits Light by Polarization"; PhysicsWorld.com; Nov. 7, 2006.*

* cited by examiner

*Primary Examiner* — Roy Punnoose
(74) *Attorney, Agent, or Firm* — 24IP Law Group; Timothy R. DeWitt

(57) ABSTRACT

A system and method for detection and measurement of circular birefringences in materials that exhibit the Faraday effect. The method and apparatus permit detection of optical activities via the difference in the directions of propagation the left- and the right-circularly polarized light (components). A beam of light is directed at an interface formed by the optically active medium and another medium such that a difference in the angles of refraction and/or reflection and/or diffraction between the left- and the right-circularly polarized components of the light beam can be detected. The difference in the propagation directions between the two circularly polarized light components is measured on a position sensitive detector and/or is detected as an intensity difference.

32 Claims, 26 Drawing Sheets

CIRCULAR BIREFRINGENCE REFRACTOMETER: METHOD AND APPARATUS FOR MEASURING OPTICAL ACTIVITY

CROSS-REFERENCE TO RELATED APPLICATIONS

The present application claims the benefit of the filing date of U.S. Provisional Patent Application Ser. No. 60/806,074 entitled "Circular Birefringence Refractometer: Method And Apparatus For Measuring Optical Activity" and filed on Jun. 28, 2006 by inventors Peer Fischer and Ambarish Gosh.

STATEMENT REGARDING FEDERALLY FUNDED RESEARCH

None.

BACKGROUND OF THE INVENTION

1. Field of the Invention

The present invention relates to systems and methods for detection and measurement of circular birefringences in materials, such as optically active (chiral) liquids and materials that exhibit the Faraday effect.

2. Brief Description of the Related Art

An isotropic optically active medium, such as a chiral liquid, is characterized by a difference in the refractive indices for left- and right-circularly polarized light. This refractive index difference is known as circular birefringence and gives rise to the rotation of the plane of polarization of a linearly polarized light beam traversing the medium. Optical rotation only arises in an isotropic medium, such as a liquid, if the medium is chiral. The measurement of optical rotation in an isotropic medium (in the absence of a static magnetic field) is therefore a measure of the presence of chiral molecules and is the basis of standard laboratory instruments such as polarimeters. The optical rotation measured in polarimeters is directly proportional to the distance the light traverses through the sample. See Barron, L. D. Molecular light scattering and optical activity (Cambridge University Press, Cambridge, 2004).

There is a need to measure optical activities—such as those that are due to chiral molecules—without the need for long path-lengths, e.g. in small volumes. By measuring a property that is a function of the relative difference in the direction of propagation of the two circularly polarized light components, rather than the rotation of the plane of polarization, the present invention shows that optical activities can be determined in an alternate way that is not a function of the distance the light traverses through the sample. An apparatus based on the principle detailed in the present invention may therefore be used to determine the optical activity, enantiomeric excess, optical purity, chemical composition, etc. of a small volume of liquid, gas, or solid, and can therefore form the basis for a detector of, say chiral analytes in suitable capillaries, liquid drops etc.

The invention is based on a difference in the angles of refraction between the two circularly polarized light components that refract at an interface in the presence of circular birefringence and/or a difference in the angles of reflection between the two circularly polarized light components that reflect at an interface formed by the medium that exhibits circular birefringence and a suitable reflector. Similar phenomena may also be observed in diffraction. First, these principles are applied to the measurement of natural optical activity (chiral liquids), then it is shown how the same principles also apply to optical activity as is induced by a magnetic field (Faraday effect).

In general, light refracts and its speed and direction can change as it traverses the boundary between two (at least partly) transparent media. Should a material be characterized by polarization-dependent refractive indices, then the different polarization components of a wave refract differently. This phenomenon, known as double refraction or birefringence, is found in many anisotropic media, such as crystals, where it may cause a ray of light to separate into two. See Born, M. & Wolf, E. Principles of Optics (Cambridge University Press, Cambridge, 1999) and Ditchburn, R. W. Light (Dover, N.Y., 1991). Isotropic media, such as a liquid or a gas, can only give rise to double refraction if they are distinct from their mirror image (are chiral) and thus optically active. Because of a difference in refractive indices for left- and right-circularly polarized light, linearly polarized or unpolarized light entering an isotropic optically active medium at an angle, will split into two waves at the boundary, one left- and the other right-circularly polarized, with a small difference in the respective angles of refraction. See Fresnel, A. J. in Euvres complètes d' Augustin Fresnel (eds. Sénarmont, H. de, Verdet, É. & Fresnel, L.) (Paris, 1866); Fresnel, A. *Ann. Chim. Phys.* 28, 147 (1825); and Lowry, T. M. Optical rotatory power (Dover, N.Y., 1964). The doubling of a linear or unpolarized light beam into its circular polarization components after traversing the interface(s) formed by an optically active medium have been reported to have been observed, both via multiple-refractions in a chiral liquid (E. v. Fleischl, "Die doppelte Brechung des Lichtes in Flüssigkeiten,"*Sitz. Ber. Kais. Akad. Wiss.* (*Math-Nat*) 90, (1884), 478), as well as via multiple-reflections in a Faraday medium (D. B. Brace, "On the resolution of light into its circular components in the Faraday effect", *Phil. Mag.* 6, (1885), 464-475). Essentially a single beam of light is observed to double. This, however, is a relatively impractical and insensitive scheme to measure circular birefringences. Much more sensitive are the schemes that form the basis of the present invention.

The apparatus and methods of this invention show that instead of taking a picture of a single light beam forming a double image, it is more practical and sensitive to detect the position of a light beam on a position sensitive detector as the light is modulated between left- and right-circular polarized. The apparatus and methods of this invention can be observed at a single interface, do not require large sample volumes, and are readily implemented. (See Ghosh, A., and Fischer, P., "Chiral molecules split light: reflection and refraction in a chiral liquid", Phys. Rev. Letters 97 (2007) 173002.)

It is shown that the difference in propagation directions (angular divergence) measured using the present invention can be used to sensitively determine the optical purity (enantiomeric excess) of a chiral liquid. The angular divergence between the two refracted circularly polarized waves contains information identical to that obtained from conventional optical rotation measurements. However, unlike optical rotation, which depends on the path length through the sample, chiral double refraction, as this phenomenon may be termed, arises within a few wavelengths from the boundary.

Isotropic media, such as liquids, composed of randomly oriented molecules are, in the absence of an external influence generally described by a single scalar refractive index. It follows that there is only one refracted beam and only one angle of refraction. This is given by Snell's law (See Hecht, E., "Optics", Addison Wesley, 2004):

$$n_1 \sin \theta_1 = n_2 \sin \theta_2, \quad (1)$$

where the angle the beam makes with the normal of the interface is $\theta_1$ in the medium with refractive index $n_1$ and similarly $\theta_2$ is the angle the beam makes with the normal of the interface in the medium with $n_2$. It therefore follows that light incident on an interface formed by two isotropic media 1 and 2 with angle of incidence $\theta_1$ in medium 1 will change its direction, i.e. refract in medium 2, where its angle of refraction is given by $$\theta_2 = \arcsin\left(\frac{n_1}{n_2}\sin\theta_1\right). \quad (2)$$

Optically active media have the power to rotate the polarization of a linearly polarized light beam. Of particular interest are media that have this property even when they are isotropic, i.e. in the absence of any strain, (quasi) static fields, or other perturbations that could cause the dielectric function to become direction dependent. Such optically active media that do not have a direction dependent dielectric function (refractive indices) and therefore do not have just one scalar refractive index, can be characterized by two refractive indices, one for left- (−) and one for right- (+) circularly polarized radiation. Note, that linearly polarized light may be regarded as a coherent superposition of left- and right-circularly polarized waves of equal amplitude, and Fresnel's theory of optical rotation shows that a difference in the respective refractive indices $n^{(-)}$ and $n^{(+)}$ causes the waves to acquire different phases and the polarization vector to rotate. The optical rotation $\alpha$ in radians developed by light at the wavelength $\lambda$ traversing a distance d in an optically active medium, such as a chiral liquid, accordingly is:

$$\alpha = \frac{\pi d}{\lambda}(n^{(-)} - n^{(+)}) \quad (3)$$

and is a function of the circular birefringence $n^{(-)}-n^{(+)}$. See Barron, L. D. Molecular light scattering and optical activity (Cambridge University Press, Cambridge, 2004) and Hecht, E., "Optics", Addison Wesley, 2004. A significance of optical rotation lies in the fact that it is a means to distinguish the two mirror image forms (enantiomers) of a chiral molecule, since $n^{(-)}-n^{(+)}$ and hence $\alpha$ is of opposite sign for the two enantiomers. Most biologically important molecules, such as sugars, are chiral and optical rotation is a well established analytical technique used to determine their absolute stereochemical configuration (and concentration) in solution. See Povalarapu, P. L. *Chirality* 14, 768-781 (2002).

Since isotropic optically active media possess two refractive indices, their double refraction can not only manifest itself through optical rotation, but also through a difference in the corresponding angles of refraction (and similarly diffraction in a suitable transmission grating). Each circularly polarized wave, or component of a wave, will bend differently at a boundary, and these refraction events are therefore independently described by expressions analogous to Eq. (1). For instance, refraction at an interface formed by an achiral medium, such as air, with refractive index n, and an optically active medium, such as a chiral liquid, with refractive indices $n^{(+)}$ and $n^{(-)}$ for right- and left-circularly polarized light, respectively will be described by $$n \sin \theta = n^{(+)} \sin \theta^{(+)}, \quad (4)$$

and $$n \sin \theta = n^{(-)} \sin \theta^{(-)}, \quad (5)$$

where $\theta$ is the angle of incidence in the achiral medium, and where $\theta^{(+)}$ and $\theta^{(-)}$ are the angles of refraction for the right- and left-circularly polarized light components respectively. An unpolarized or a linearly polarized light beam incident on an interface described by Eqs. (4) and (5) will thus split in the chiral medium into its circular components which will travel with different angles of refraction. This is depicted schematically in FIG. 1a. An unpolarized or linearly polarized light beam 10 is incident from a medium 11 with refractive index n onto the boundary (interface) 16 formed with medium 12 that is characterized by refractive indices $n^{(+)}$ and $n^{(-)}$. The normal of the interface is 13. The two refracted circularly polarized components are 14 and 15. Alternately, as shown in FIG. 2a, if right-circularly polarized light 20 is incident on this interface, formed by media 11 and 12, then it will refract and travel in the direction 21 given by angle of refraction $\theta^{(+)}$. As seen in FIG. 2b, left-circularly polarized light 22 incident on this interface it will correspondingly take a different path 23 given by $\theta^{(-)}$.

Such splitting and/or differences in angles of refraction are also present if the light travels from the chiral medium to the achiral medium, i.e. is incident from 12 onto 11 (an chiral/achiral interface). Similarly, such splitting and/or differences in angles of refraction can be observed if the light travels from one chiral medium to another chiral medium which is characterized by a different circular birefringence. As shown in FIG. 3a, an unpolarized or linearly polarized light beam 10 that is incident normal onto a prismatic sample 30 that exhibits circular birefringence will deviate in its direction of propagation and will separate into its two circularly polarized components 14 and 15 that correspondingly exhibit an angular divergence. Should two prismatic cuvettes 30 be arranged as shown in FIG. 3b and such that 10 traverses their interface at an angle, then the two circularly polarized components 14 and 15 diverge symmetrically about 10 if the two media 31 and 32 in 30 have the same scalar refractive index $(n^{(-)}+n^{(+)})/2$, but differ only in their circular birefringence (pseudoscalar refractive index). This may for instance be achieved if the liquids in 31 and 32 only differ in their respective amounts of enantiomeric excess.

In the preferred embodiments of the present invention that are based on refraction and/or reflection the light must not be incident normal to the interface, i.e. along 13, in FIGS. 1 and 2.

The invention details how the determination of the difference between these angles of refraction and/or reflection, i.e. $\theta^{(-)}-\theta^{(+)}$, or any related such measurement, can be used as an alternative to optical rotation measurements and as a diagnostic for optical activity and therefore chirality.

A difference in the angles of reflection can occur in an optically active medium, as schematically shown in FIG. 1b, if the reflection preserves (at least some) of the circularity of the light upon reflection. Linearly polarized or unpolarized light 10 is incident from an optically active medium 110 characterized by unequal refractive indices for left and right-circularly polarized light $n^{(-)}$ and $n^{(+)}$. 10 is incident with angle of incidence $\theta$ upon a reflecting surface 17. The circular polarization components change sign upon reflection, i.e. a left-circularly polarized component will become (at least partially) right-circularly polarized upon reflection and therefore experiences a different refractive index if the medium is circular birefringent. The angle of reflection is $\theta_{refl.}^{(\pm)}$ for left (−) and right (+) circularly polarized light is given by $$\theta_{refl.}^{(\pm)} = \arcsin\left(\frac{n^{(\mp)}}{n^{(\pm)}}\sin\theta\right). \quad (6)$$

As seen in FIG. 1c, left-circularly polarized 101 and right-circularly polarized light 103 incident upon a reflecting surface 17 with the same angle of incidence θ will reflect with different angles of reflections (given by Eq. 6) and therefore propagate with different directions 102 and 104 respectively.

The invention is also applicable in situations where diffraction in an optically active medium is important. The diffraction phenomena are related to the refraction and reflection phenomena described above. For a diffraction grating of groove spacing D, the angular position, θ of the diffracted spot is given by (See Hecht, E., "Optics", Addison Wesley, 2004):

$$D\sin\theta = m\frac{\lambda_0}{n}. \quad (7)$$

Here m is the order of diffraction, $\lambda_0$ is the vacuum wavelength of light and n is the refractive index of the light in the medium where the diffraction grating is placed. Since the refractive indices of right and left circularly polarized light are different in an optically active medium, the angular positions of the diffracted spots are also different. The angular deviation between the right and left circularly polarized light after diffraction is given by (Ambarish Ghosh, Furqan Fazal, and Peer Fischer, "Circular differential double diffraction in chiral media", *Optics Letters*, (2007), Doc. ID 81432):

$$\theta^{(+)} - \theta^{(-)} = \arcsin\left(\frac{m\lambda_0}{Dn^{(+)}}\right) - \arcsin\left(\frac{m\lambda_0}{Dn^{(-)}}\right) \quad (8)$$

Consequently, a measurement of the angular deviation between the two light beams provides a direct measure of the optical activity of the liquid. This or a similar analysis applies for diffraction in transmission or reflection.

The application of a magnetic field in the direction of propagation of a light beam renders all media optically active, i.e. causes circular birefringence. However, these media are also anisotropic. The anisotropy means that the light propagation is in general described by effects in addition to those that are due to circular birefringence. Nevertheless, if these additional effects may be neglected, or if they are small, or if the magnetic field has a component along the direction of propagation of the light beam, then phenomena essentially similar to those due to chirality and described above can be observed ("Observation of the Faraday effect via beam deflection in a longitudinal magnetic field", Ambarish Ghosh, and Peer Fischer, eprint arXiv:physics/0702063, 2007). The magnetic field induced effects differ from the effects in chiral liquids in that they are unrelated to molecular chirality and in that they depend on the relative direction between propagation direction and magnetic field direction. However, for a field along the propagation direction, the circular birefringence induced is given by $$\alpha = \frac{\pi d}{\lambda}(n^{(-)} - n^{(+)}) = VBd \quad (9)$$

where V is the Verdet constant and B the magnetic field strength. The difference in the angles of refraction and reflection and diffraction for circularly polarized light components due to the Faraday effect are essentially the same as those (see above) obtained for chiral samples. See also ("Observation of the Faraday effect via beam deflection in a longitudinal magnetic field", Ambarish Ghosh, and Peer Fischer, eprint arXiv: physics/0702063, 2007).

SUMMARY OF THE INVENTION

The present invention describes a method and an apparatus that can be used to determine the optical activity of a medium. The circular birefringence of an optically active medium, such as a chiral liquid, can give rise to differences in the angles of refraction (and/or reflection and/or diffraction) for left- and right-circularly polarized light (components) and it is detailed how this can be used to measure and quantify optical activity. In essence, it is shown that either the separation, i.e., splitting, between the left- and right-circularly polarized light (components) or the difference in the respective angles of refraction (and/or reflection and/or diffraction) of left- and right-circularly polarized light (components) at a suitable interface can be used to determine a medium's optical activity. The method presents an alternative to optical rotation measurements (polarimetry). In particular, the invention may be used to establish the handedness (enantiomeric excess, or optical purity) etc. of a chiral liquid, a solution of molecules that is distinct from its mirror image. Unlike optical rotation, the method of the present invention does not directly depend on pathlength through the optically active medium. Moreover, as refraction (reflection, diffraction) takes place within a few wavelengths from the interface, the invention is therefore especially promising for the measurement of optical activities in small volumes, such as liquids in capillaries, and microfluidic devices, thin films, etc.

The invention may also be used to determine optical activities that are induced by a magnetic field as in the Faraday effect, and thereby be used to measure Verdet constants and related magneto-optical properties, as well as magnetic fields when a material of known Verdet constant is used.

The invention is similarly useful in the determination of large optical activities that give rise to correspondingly large optical rotations as it does not suffer from the (multiples of π) phase ambiguity which characterizes polarimeters. It can be used in fast measurements to determine peak optical activities associated for instance those with pulsed magnetic fields.

For one, the present invention is based on a difference in the angles of refraction that left- and right-circularly polarized light experiences at an interface between an optically active and an optically inactive medium, or two media with different optical activities. The difference in the angles in refraction causes the circularly polarized components to propagate in different directions which can be recorded on a suitable detector, such as a position sensitive detector, a diode, PMT CCD, etc.

In another embodiment, an imaging device such as a (CCD) camera in conjunction with polarization modulation can be used to record the difference in propagation directions that circularly polarized light components experience after traversing an interface between an optically active and an optically inactive medium, or two media with different optical activities.

In yet another embodiment, the optically active medium is in direct contact with a reflecting surface. The circularly polarized light components in the optically active medium reflect with different angles of reflection. At the mirror the circular components experience a difference in their directions of propagation. This is detected with a suitable detector.

Several embodiments detail how the difference in the directions of propagation of the two circularly polarized light components in an optically active medium can be increased in geometries that permit multiple such refraction events and/or suitable reflections and/or diffractions.

The present invention will be particularly useful in measuring the optical activity of small liquid volumes. The technique is suitable for miniaturization, and will therefore work even at length scales when diffraction effects become important. The angular divergence between the left- and right-circular polarization components depends on the wavelength of light in a medium and therefore the refractive index, and not the path-length traversed through the medium. It follows that miniaturization of the sample cell containing the optically active and the refraction/reflection/diffraction optics giving rise to the effect of this invention to micron-sized (or less) dimensions should be possible without any loss in the observed angular deviation between the two circularly polarized light beams.

In a preferred embodiment, the present invention is an apparatus for measuring circular birefringence of an optically active medium which exhibits circular birefringence either due to chirality and/or induced by a magnetic field. The apparatus comprises a container for holding a sample of an optically active medium such that it forms an interface with another medium, a light source from which a light beam is incident upon said interface, such that said light beam refracts and/or reflects and/or diffracts at said interface, a means for controlling and manipulating the polarization of said light beam either before and/or after said sample, and a detector upon which said reflected and/or refracted and/or diffracted light beam is incident which is furthermore sensitive to a difference in the propagation direction of left and right circularly polarized light components of said refracted and/or reflected and/or diffracted light beam.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE INVENTION

Figure 2A:
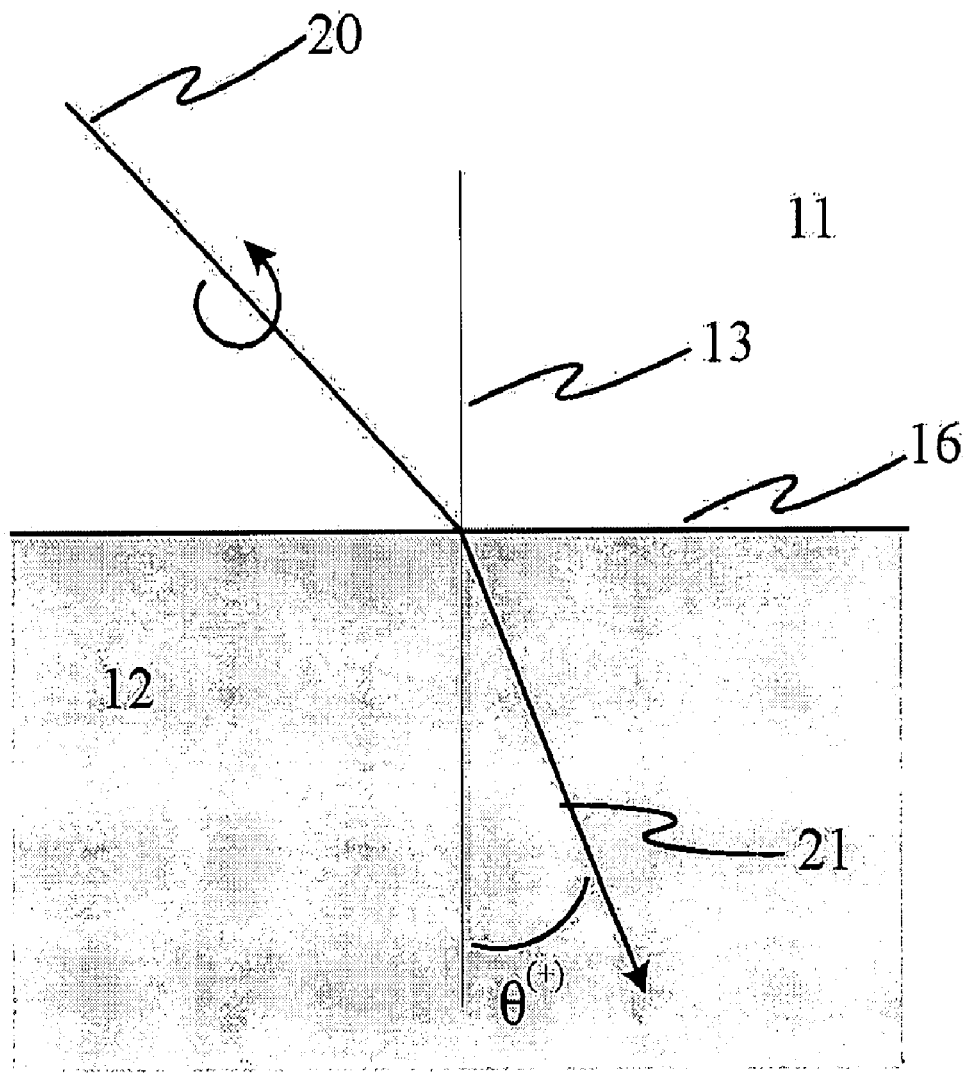
FIG. 2a is a schematic depiction of the refraction for the right-circularly polarized beam.
Figure 2B:
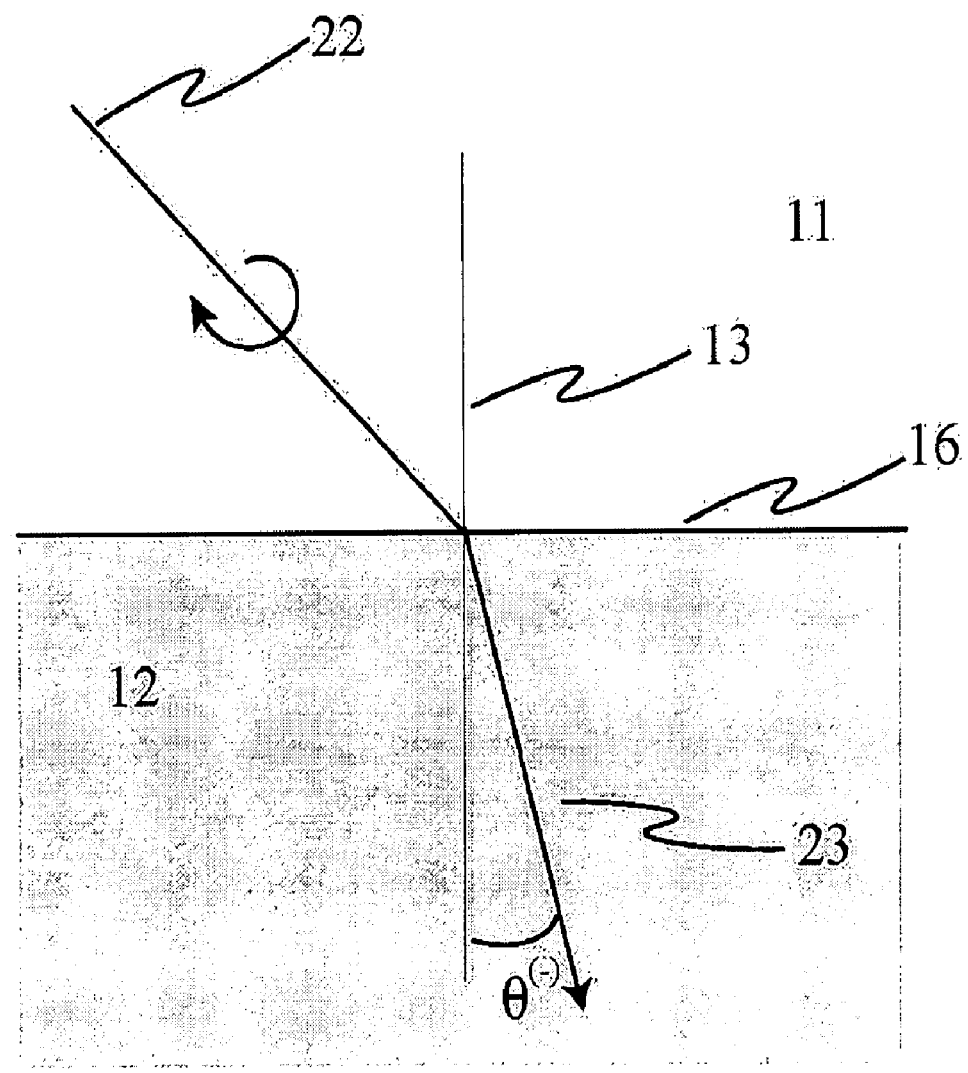
FIG. 2b is a schematic depiction of the refraction for the left-circularly polarized beam.
Figure 3A:
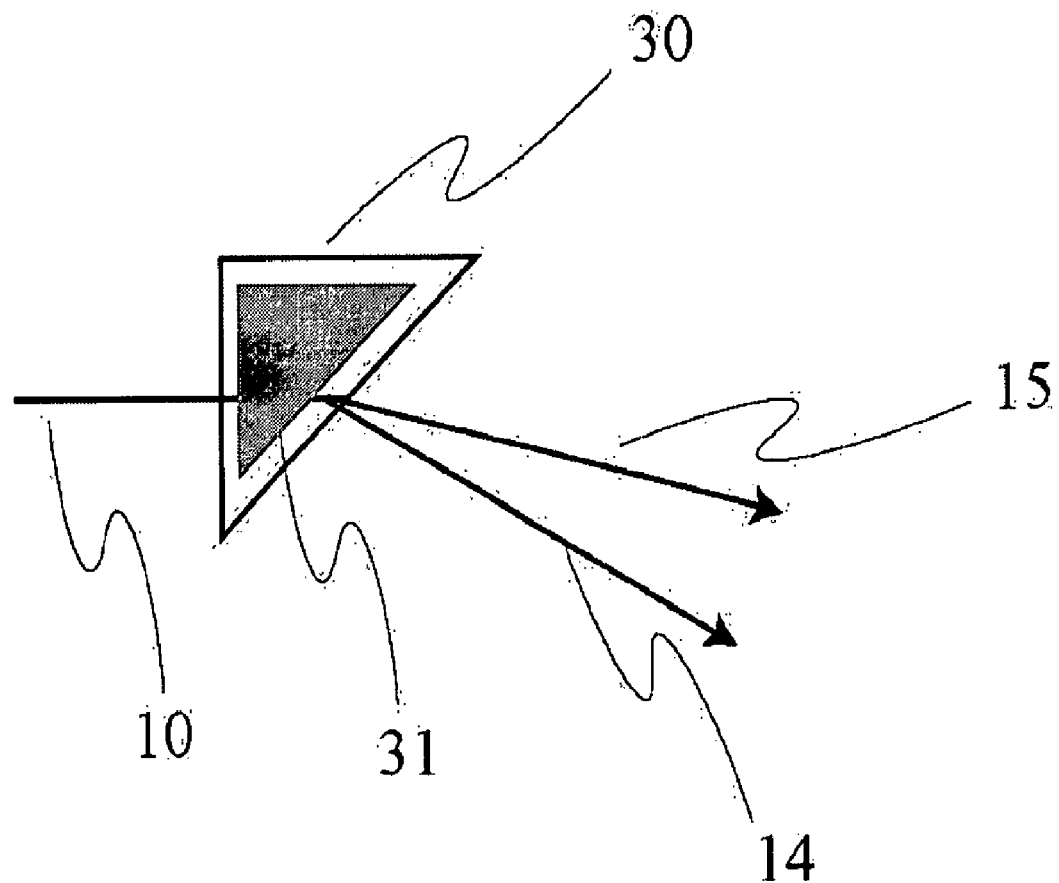
FIG. 3a is a drawing of a prism or a prismatic cuvette and a light beam as it enters the prism. If the prism contains a chiral liquid, then the light beam will separate as shown as it exits into the surrounding medium, possibly air. The same effect can be expected from a light beam that enters a material in the presence of a magnetic field parallel to the incident beam. In both cases the incident light beam is unpolarized or linearly polarized. As in FIGS. 1 and 2, the separation is not to scale. For small differences in the two angles of refraction between the left- and the right-circularly polarized beam, these two beams will (partially) overlap.
Figure 4A:
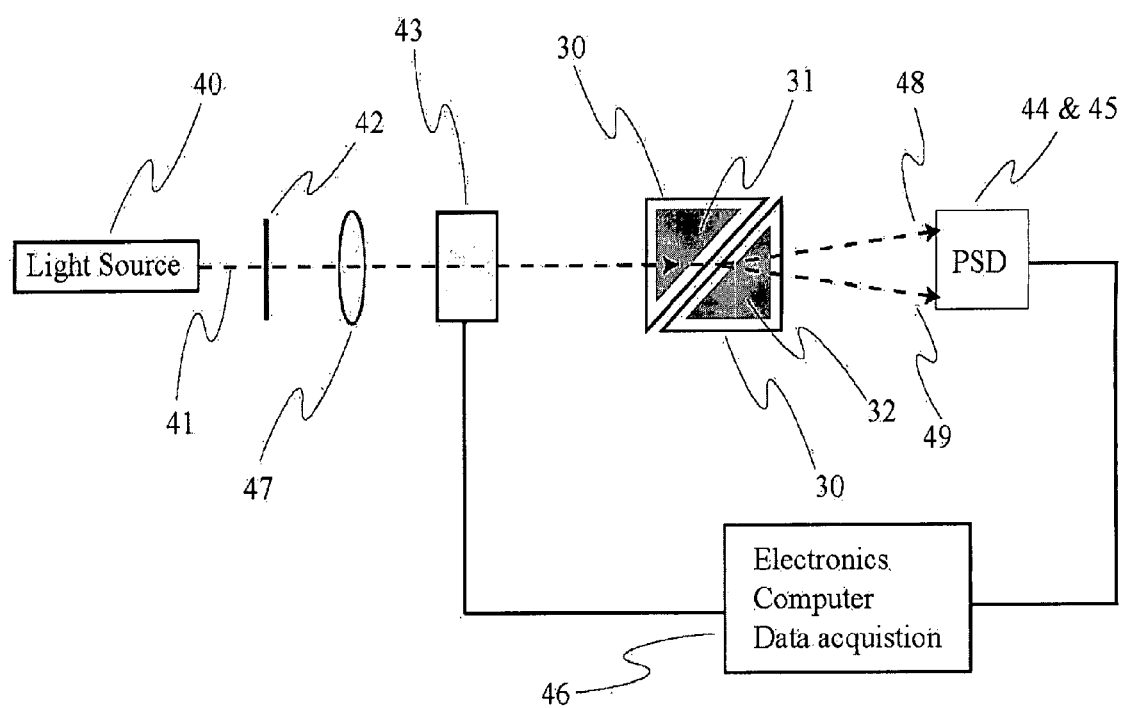
FIG. 4a is a drawing of a possible embodiment of the invention as it pertains to the measurement of optical activities (chirality) in a liquid sample.
Figure 4B:
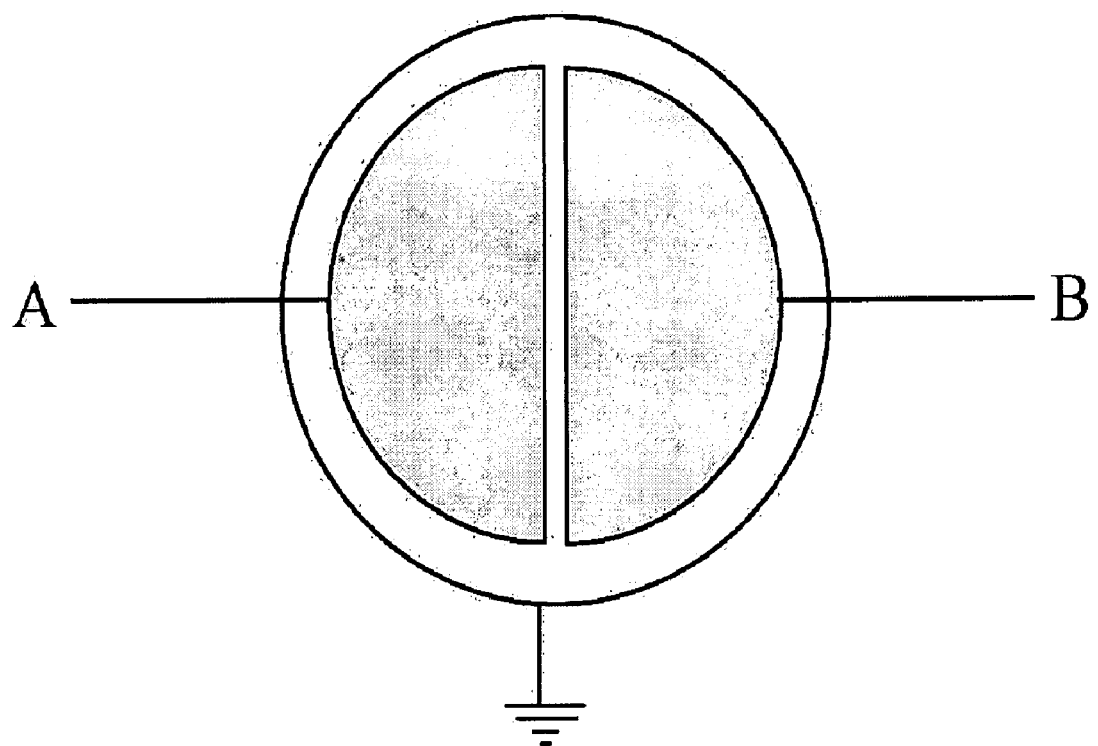
FIG. 4b and FIG. 4c show position sensitive detectors that can be used to locate the position of a light beam striking the active area of these detectors.
Figure 4C:
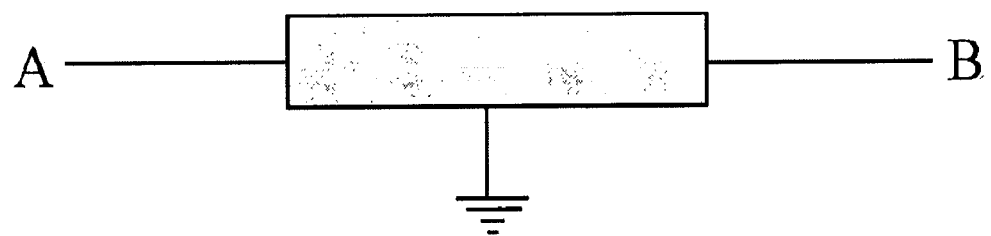
Figure 8A:
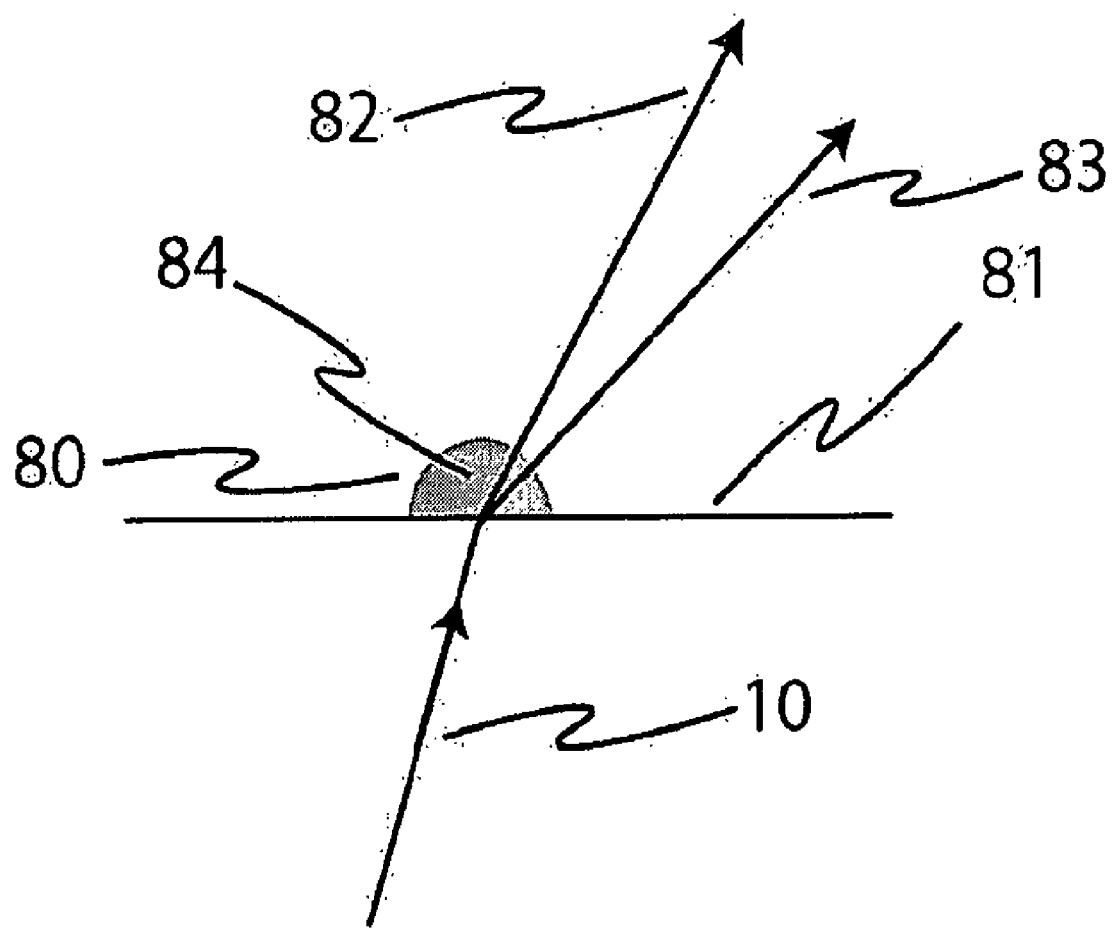
FIGS. 8a-c show sample geometries that permit the observation of the difference in angles of refraction at an interface formed by a circularly birefringent medium, such as a chiral liquid. The use of an incoherent light source could help in minimizing possible interference phenomena as could the use of anti-reflection coatings at suitable surfaces.
Figure 8B:
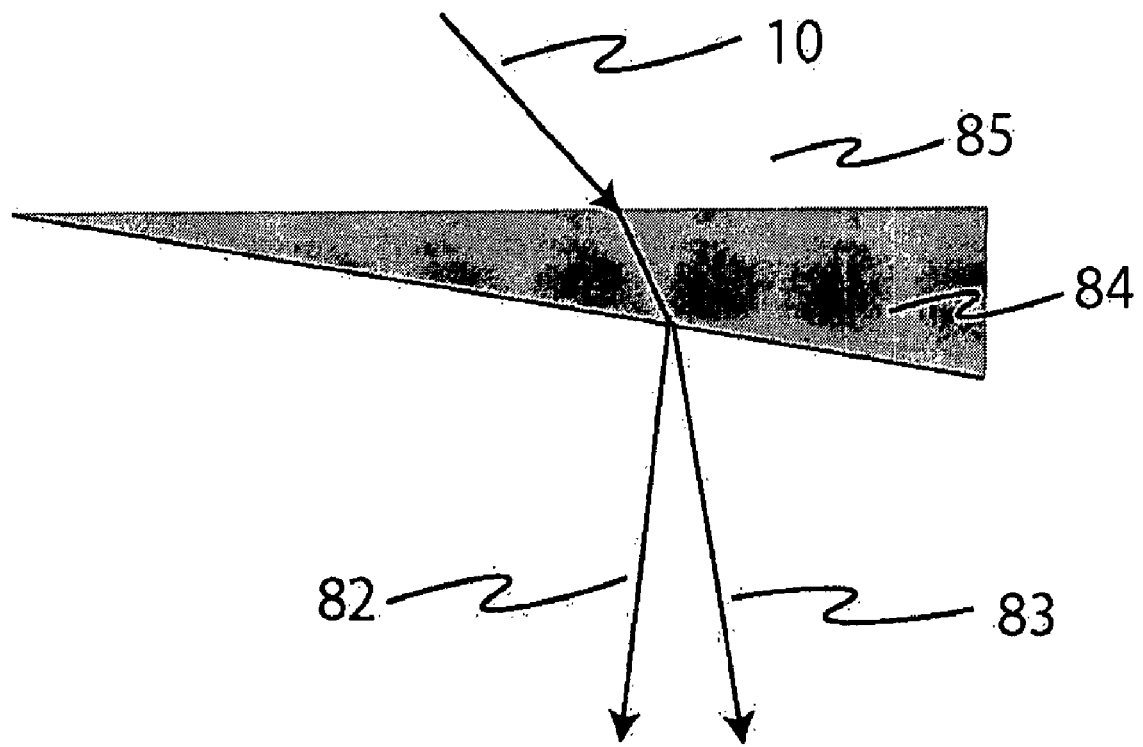
Figure 8C:
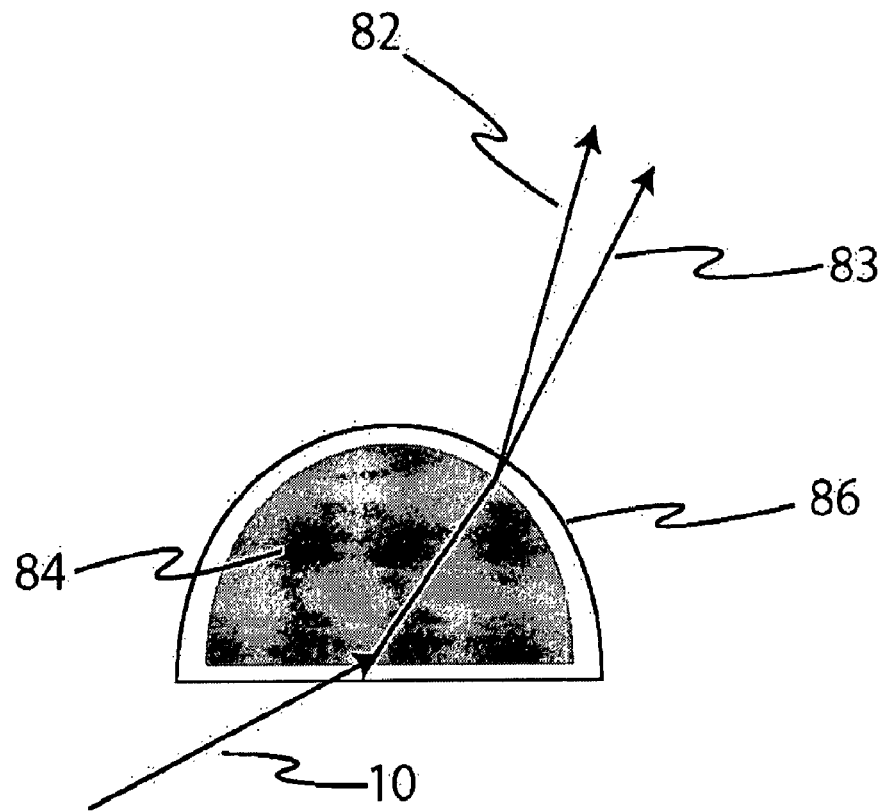
Figure 9A:
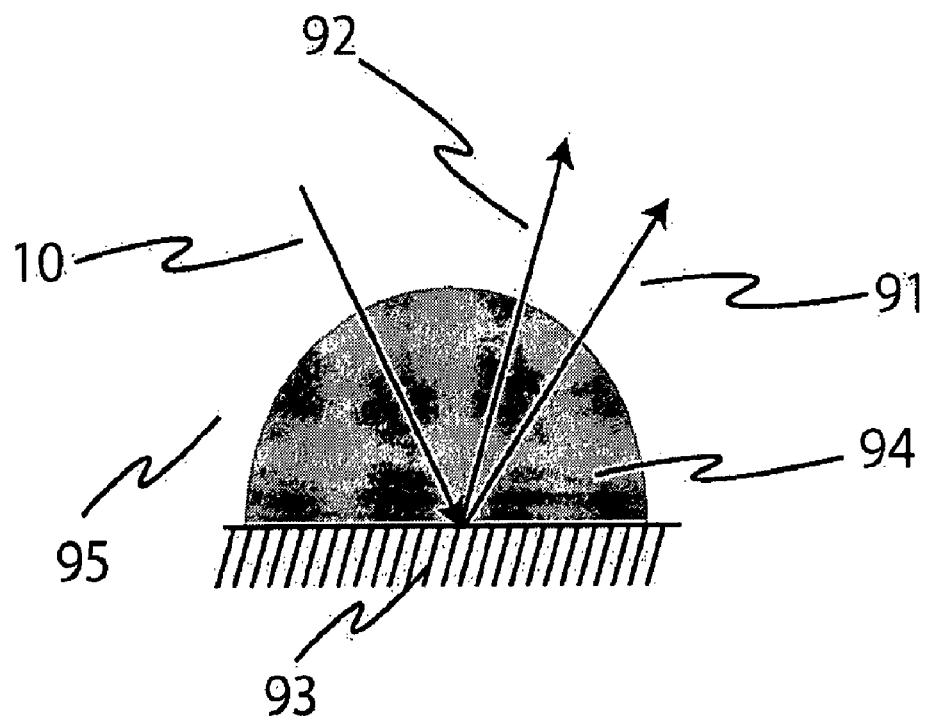
FIGS. 9a-d show sample geometries that permit the observation of the difference in angles of reflection of a light beam in a circularly birefringent medium, such as a chiral liquid, in contact with a reflecting surface. As the unpolarized or linearly polarized light beam enters the optically active medium it's circularly polarization components travel along the same direction. After the reflection at the reflective surface their respective circularities reverse, i.e. the right-circularly polarized component becomes left-circularly polarized and vice versa. At the second refraction, the "exit" surface the circularly polarized components may also refract. Any optical rotations due to chirality are likely to be small (possibly zero). The saw-tooth shaped surface in FIG. 9c may be obtained using a surface from or similar to those used in Fresnel lenses, or by using grating surfaces, or by microfabrication techniques, such as asymmetric etching of a single-crystalline Silicon substrate, etc.
Figure 9B:
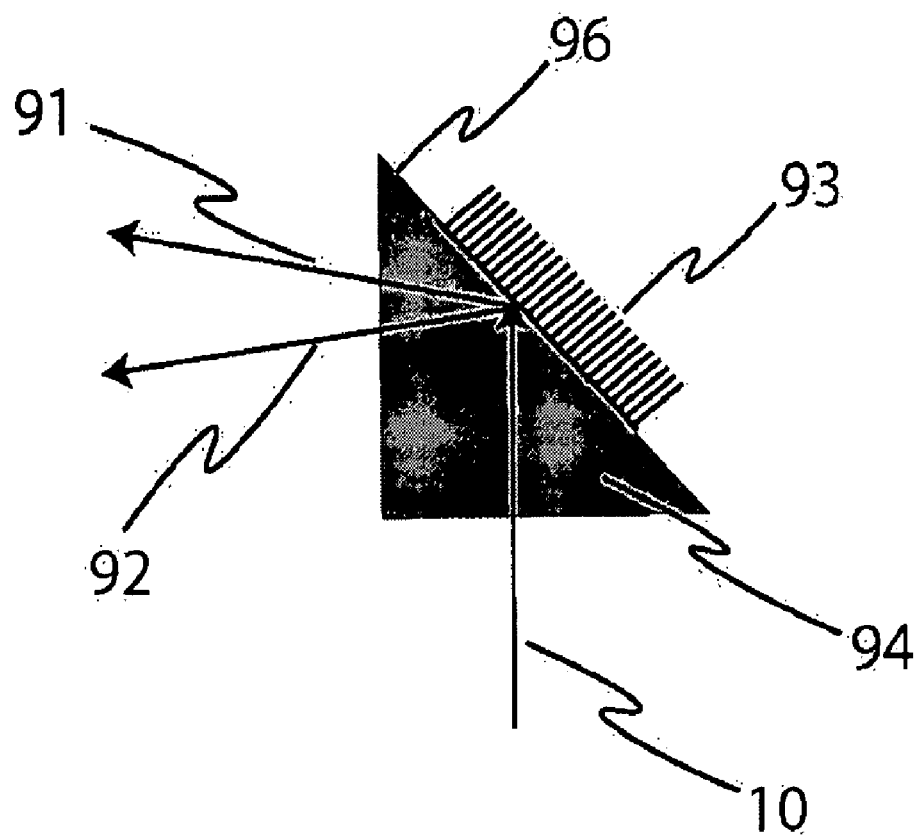
Figure 9C:
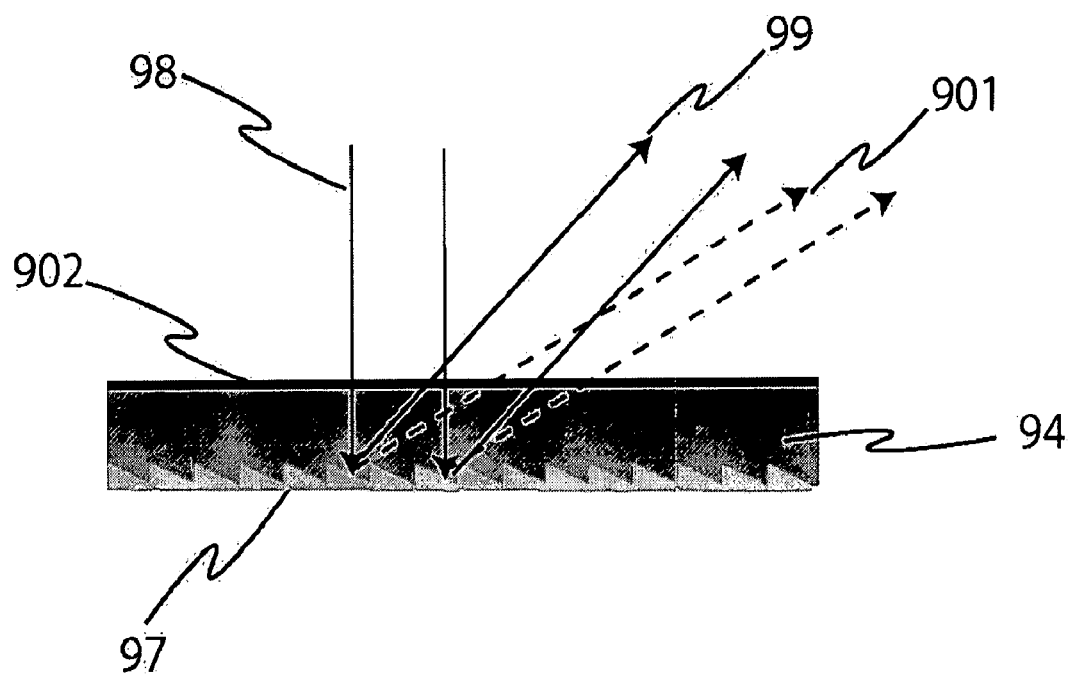

An apparatus in accordance with one embodiment of the invention is shown in FIG. 4a and consists of a light source 40 such as a laser that emits light which is collimated such that it forms a beam 41. In other embodiments a lamp or in yet another embodiment a light emitting diode may be used together with suitable optics such a lens or a lens-system 47. These light sources may be used at different parts of the electromagnetic spectrum and may be coupled with a monochromater to select a particular wavelength. Said light is then in one embodiment linearly polarized by a polarizer 42 or some suitable combination of polarization optics before it is incident onto a polarization modulator 43 such as a photoelastic modulator (PEM), such as a HINDS Type II FS47. If the light is incident with the correct angle of polarization with respect to the axes of the PEM, the state of the light polarization will modulate, including from left- to right-circularly polarized. In another embodiment the light may be rendered alternately left- and right-circularly polarized by an electro-optic modulator such as a Pockels cell, or rotating polarization optics, or a liquid crystal modulator, or a combination thereof possibly in combination with other optical components. After said modulator 43 the light traverses an interface that according to FIG. 2 gives rise to a difference in the directions of propagation of the left- and right-circularly polarized components, for instance in an arrangement formed by two prismatic cuvettes 30, e.g. Sturna cells 4-TB-Q-10 contacted with index matching fluid, filled with liquids 31 and 32 that are distinguished by the circular birefringence that is to be determined. For instance 31 is a suitable achiral reference compound, or a racemic mixture of the liquid, and 32 which has some enantiomeric excess that is to be determined. Alternately, the optically active sample is contained in a cell 30 shown in FIG. 3a, or in the form of a drop 84 as shown in FIG. 8a, or in an asymmetric film or liquid volume 84 as shown in FIG. 8b, or a in a hollow capillary 86 as shown in FIG. 8c, or in a microfluidic cell as shown in FIG. 9c, etc. Regardless of the sample container and precise shape of the optically active sample, the position sensitive detector 44 records the position of the beam that refracts at an interface formed by the optically active sample, such that the circular components of the beam strike a position sensitive photodetector at different positions on the detector. The output of photodetector 44 is a current proportional to the position of the light beam incident on the detector, provided the response time of the detector electronics is faster than rate at which the light is being modulated. The two refracted circular polarization components are shown in FIG. 4a, but in reality only one of the circular components 48 and 49 is present at any one time, as 41 is polarization modulated, i.e. 48 and 49 will alternately hit the detector at respectively different positions. If 48 strikes the detector at a position $P_1$ then subsequently 49 will strike the detector at a different position $P_2$, before 48 will again strike the detector at $P_1$, and so on. Electronics circuitry 45 is used to measure the position on a segment detector, such as UDT SPOT-9D, shown schematically in FIG. 4b, or a position sensitive diode, UDT SL5-1, shown schematically in FIG. 4c. The two current outputs, A and B, from the detector are converted to voltages, $V_A$ and $V_B$, using a current to voltage converter (not shown). A differential amplifier (not shown) is used to amplify the difference of $V_A$ and $V_B$, which is then fed into the input of a lockin amplifier (Stanford Research, SR830). The component of $(V_A-V_B)$ at the reference frequency f (obtained from the photoelastic modulator), is the signal $(V_A-V_B)_f$ measured by the lockin amplifier. A separate circuit (not shown) is used to amplify the sum of $V_A$ and $V_B$, which is either measured by a data acquisition card (National Instruments, PCI-6259) or the auxiliary input of the lockin amplifier. The position of the beam, which is proportional to $(V_A-V_B)/(V_A+V_B)$, is obtained by dividing $(V_A-V_B)_f$ by the sum of voltages $(V_A+V_B)$, either in a computer, a divider circuit, or in the lockin amplifier. In another embodiment of the invention a computer with data acquisition board is used as a digital lockin to process the data.

Figure 5A:
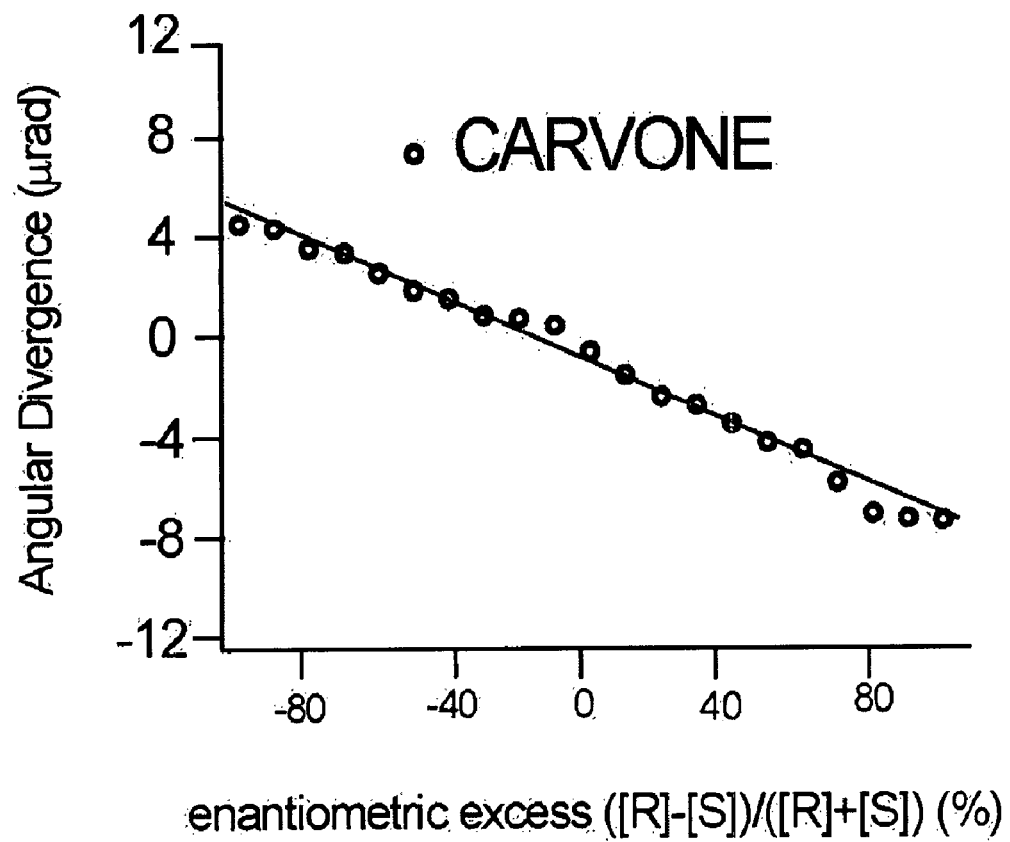
FIG. 5a is a graph showing measurement of the difference in angles of refraction in carvone, i.e., the angular divergence between the left- and the right-circularly polarized beams as a function of the enantiomeric excess is plotted.

As the enantiomeric excess (handedness, chirality) of the liquid is changed in one of the cuvettes 30, or in a similar sample holder, by means of a suitable pump, flow or titration system (not shown) the relative position between the left- and right-circularly polarized beams incident on the detector changes and this is typically measured by the lockin (not shown), or computer with data acquisition capabilities 46 and can be recorded by a computer. Data associated with such a measurement is shown in FIG. 5a where the angular divergence δ is shown as a function of the concentration difference between the two enantiomers, denoted by R and S, respectively, for carvone (Sigma Aldrich) (data red squares). The straight line is a guide to the eye. The sign for the divergence was derived from the phase relationship between the lock-in signal and the photo-elastic modulator (PEM) reference. In accord with optical rotation data (see FIG. 5b), the sign of δ depends linearly on the enantiomeric purity. Inaccuracies in pipetting small volumes and a non-zero background are the reason for the deviation from the straight line and its offset from 0. If the modulator, such as the PEM, affects the direction of the left- and right-circularly polarized components, then the signals need to be corrected for by a suitable background correction scheme or a measurement scheme that permits the background to be monitored and recorded (not used here and not shown).

Figure 5B:
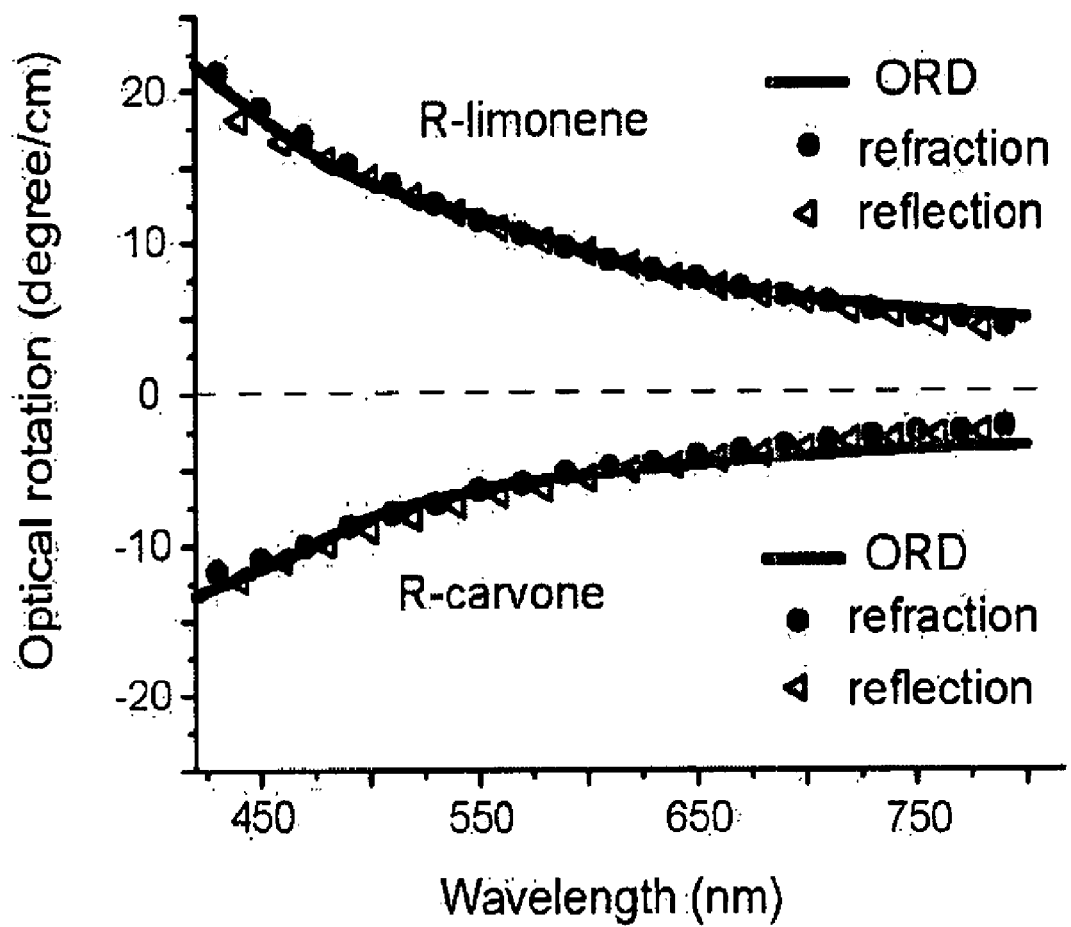
FIG. 5b is a graph showing measurement of optical rotation (optical rotatory dispersion, ORD) via traditional polarimetric methods (solid lines) as well as via the method of the present invention, i.e. the difference in angles of refraction (full circles) as well as reflection (hollow triangles) as function of wavelength for R-limonene (upper data) and R-carvone (bottom data).

FIG. 5b shows data recorded in a preferred embodiment of the invention according to FIG. 4a where the light source 40 consists of a lamp and monochromator, and the position was recorded by a UDT SPOT-9D detector. The optical rotatory dispersion (ORD) data that is shown was deduced from the wavelength-dependence of the angular divergence of the left- and right-circularly polarized light. The data for R-limonene (upper data) and R-carvone (lower data) is derived from a measurement in accord with a preferred embodiment of the present invention. The solid lines correspond to conventional optical rotation measurements and are shown for comparison. The optical rotation can be determined from the angular divergence $\delta \equiv \theta^{(+)} - \theta^{(-)}$ between the refracted beams according to the following procedure: Given that the circular birefringence to be determined is small $(n^{(-)} - n^{(+)}) \ll n$, the divergence can be written as:

$$\delta \approx \frac{\tan\theta}{n}(n^{(-)} - n^{(+)}), \quad (9)$$

where $n = (n^{(-)} + n^{(+)})/2$ and where $\theta$ is the average of the two angles of refraction. The refractive index n can be obtained from the time-averaged position on the detector in a measurement scheme as shown in FIG. 4a. From the determined circular birefringence the optical rotation can now be determined with the help of Eq. (3). Similarly, the optical rotatory dispersion may be determined from measurements in reflection (data triangles), where the sample cell in FIG. 4a is replaced with a reflecting sample cell, such the one depicted in FIG. 9b. Specifically, for the data in FIG. 5b a triangular cuvette was used and the light reflected inside the cuvette at the hypotenuse of that cuvette.

Determining in addition the intensity difference between the left- and the right-circularly polarized beams enables circular dichroism measurements to be performed. A suitable experimental geometry based on the present invention can therefore be used to simultaneously measure the circular birefringence and the circular dichroism of an optically active sample.

Figure 1A:
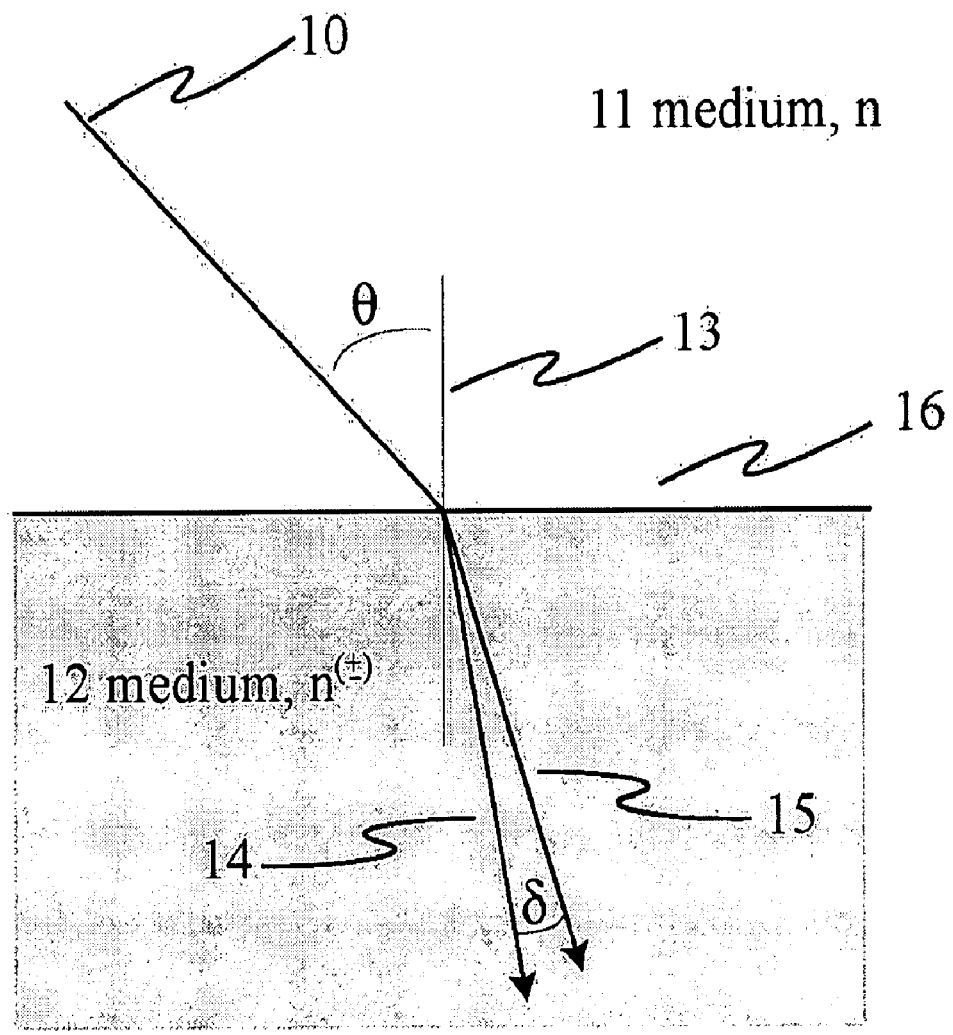
FIG. 1a is a schematic depiction the refraction of a light beam at an interface formed by a chiral isotropic medium and an achiral medium. The unpolarized or linearly polarized light beam enters an optically denser medium and splits into left- and right-circularly polarized components—the angles of refraction for the two circularly polarized beams being unequal. The angle between the refracted beams is not to scale and is likely to be on the order of microradians or less.
Figure 3B:
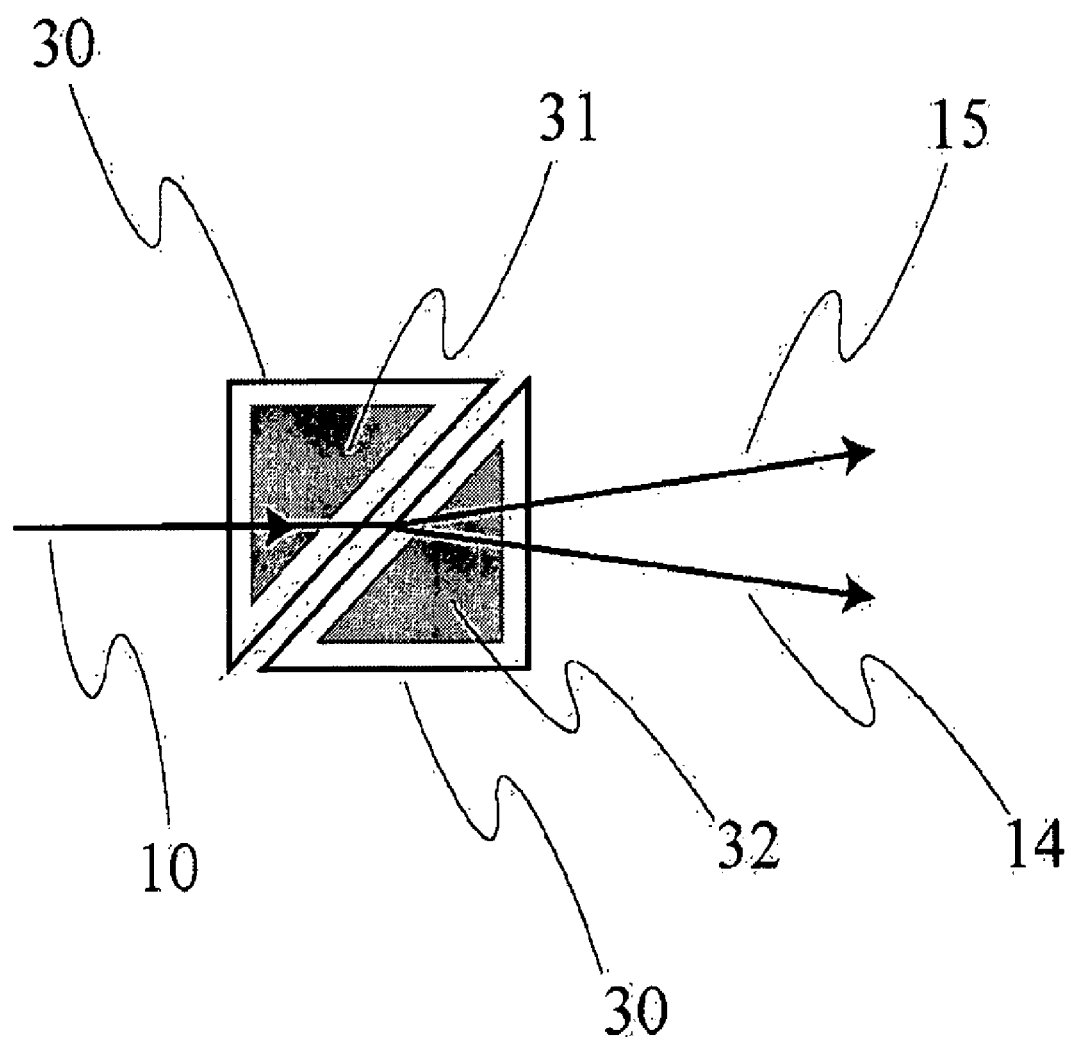
FIG. 3b is a schematic depiction of the refraction formed by two hollow prismatic cuvettes. The light beam is incident normal to the outside surface of the first prism. At the interface formed between the first cuvette and the second cuvette, presumed to contain liquids with different optical activities, but the same achiral refractive index, the unpolarized or linearly polarized light beam separates into two circularly polarized beams. The angle between the two circularly polarized wave components is a measure of the optical activities in the solutions. The schematically depicted splitting of the two polarization components is not to scale and is likely to be on the order of microradians or less. The schematically depicted refraction phenomenon could for instance be expected at an interface formed by an optically active liquid (in one cuvette) and a racemic (1:1) mixture of the two enantiomers of that chiral liquid (in the other cuvette).
Figure 6:
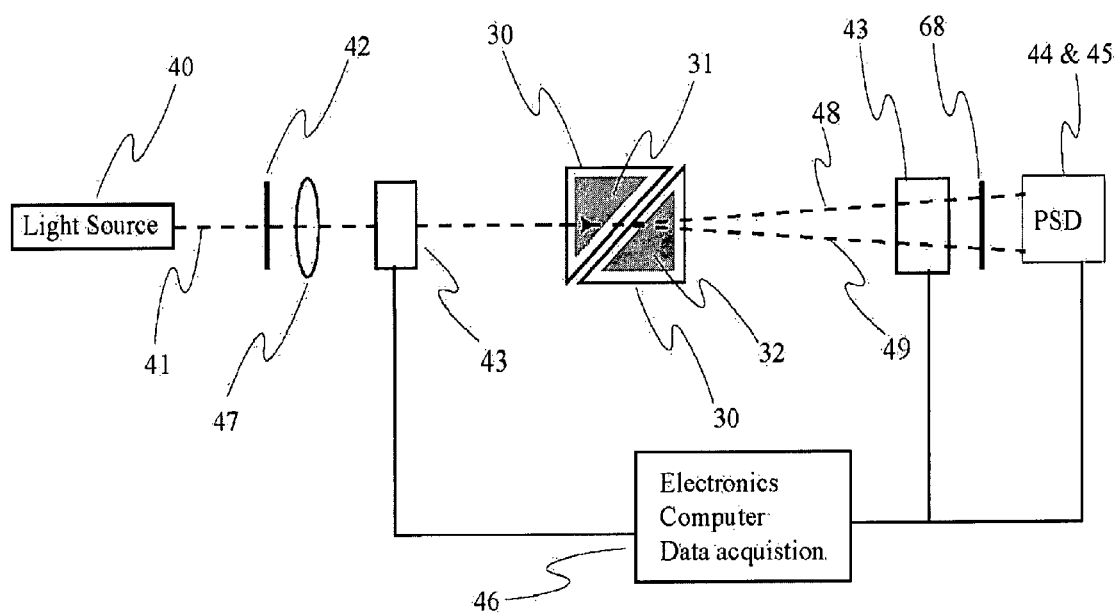
FIG. 6 is a drawing of a possible embodiment of the invention as it pertains to the measurement of optical activities (circular birefringence, chirality) in a liquid sample. Shown is a scheme that uses position sensitive detectors to phase-sensitively detect the position of a light beam that is linearly polarized as it traverses the sample. However, after the sample only the circularly polarized components of the beam are transmitted through the combination of polarization modulator and polarizer. These are position sensitively detected. Only one circular component will strike the detector at any one time, as the polarization is modulated.

An apparatus in another preferred embodiment of the invention is shown in FIG. 6 and differs from that in FIG. 4a in that the light beam 41 is linearly polarized when it is incident on the sample cells 30. The cells 30 may again be replaced with other suitable sample holders that contain an optically active samples, such as those shown in FIGS. 3a, 8, 9e. In the presence of circular birefringence or optical activity in accord with the application of the present invention, the light will separate into its circularly polarized components as shown schematically in FIGS. 1a and 3, where the splitting is not drawn to scale. Typically, the separation between the two circularly polarized components is small, microradians or less, and so a single beam will only be visible to the eye. However, the position sensitive photodetector 44 and electronics 45 together with phase sensitive detection 46 discerns, in a preferred embodiment of the present invention, the difference in the positions of the two circularly polarized components which are first rendered linearly polarized (alternately vertical and horizontal) by the polarization modulator 43 (set to give quarter-wave retardation) and which pass the polarizer 68 set to extinguish light polarized in the direction defined by the orientation of 42. For instance the polarizer 42 is set such that the light after traversing the sample cell is polarized 0 degrees with respect to the axis of the modulator 43. The modulator will pass the linear component of the light but will render any circularly polarized light linearly polarized alternating between +45 and −45 degree with respect to its axis. 68 is then set to 90 degree such that it does not pass the light that is polarized along the axis of the modulator (along 0 degree). It follows that any left- and right-circularly polarized components 48 and 49 present in the light after the cuvettes 30 will be alternately incident on different positions at the position sensitive detector 44.

Figure 7A:
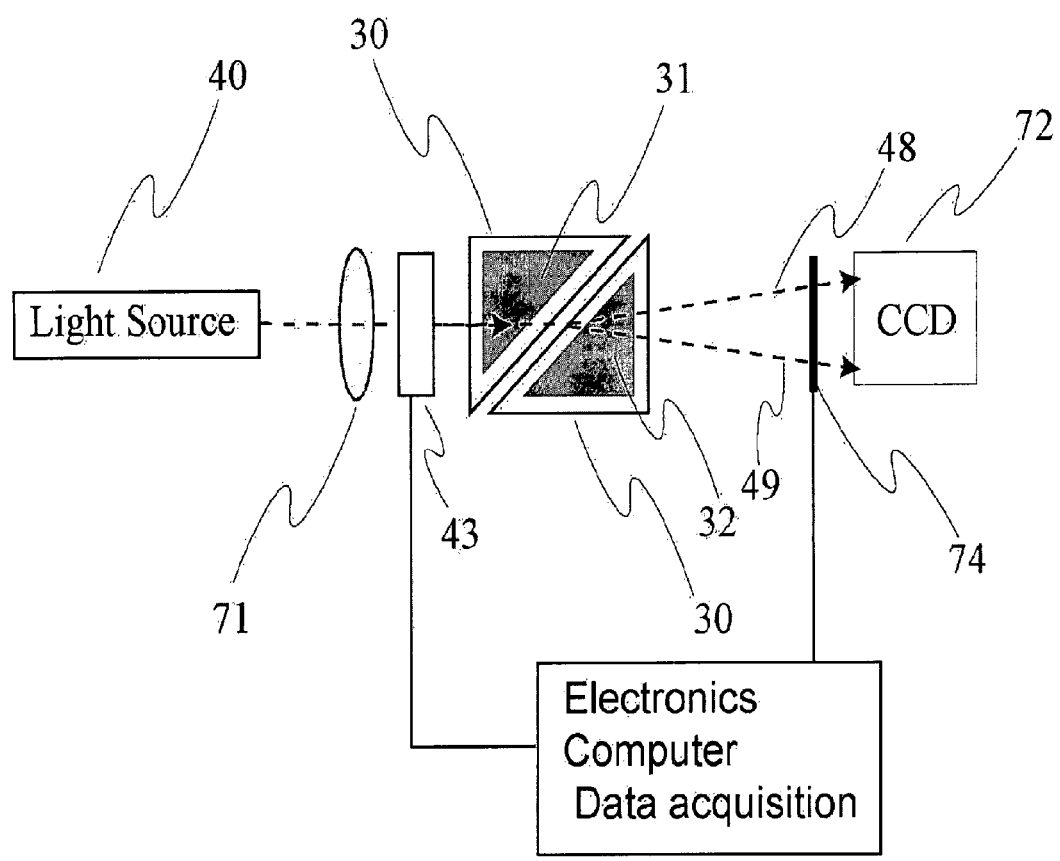
FIG. 7a shows a scheme to image the polarization dependent change in propagation direction of light on an imaging detector.
Figure 7B:
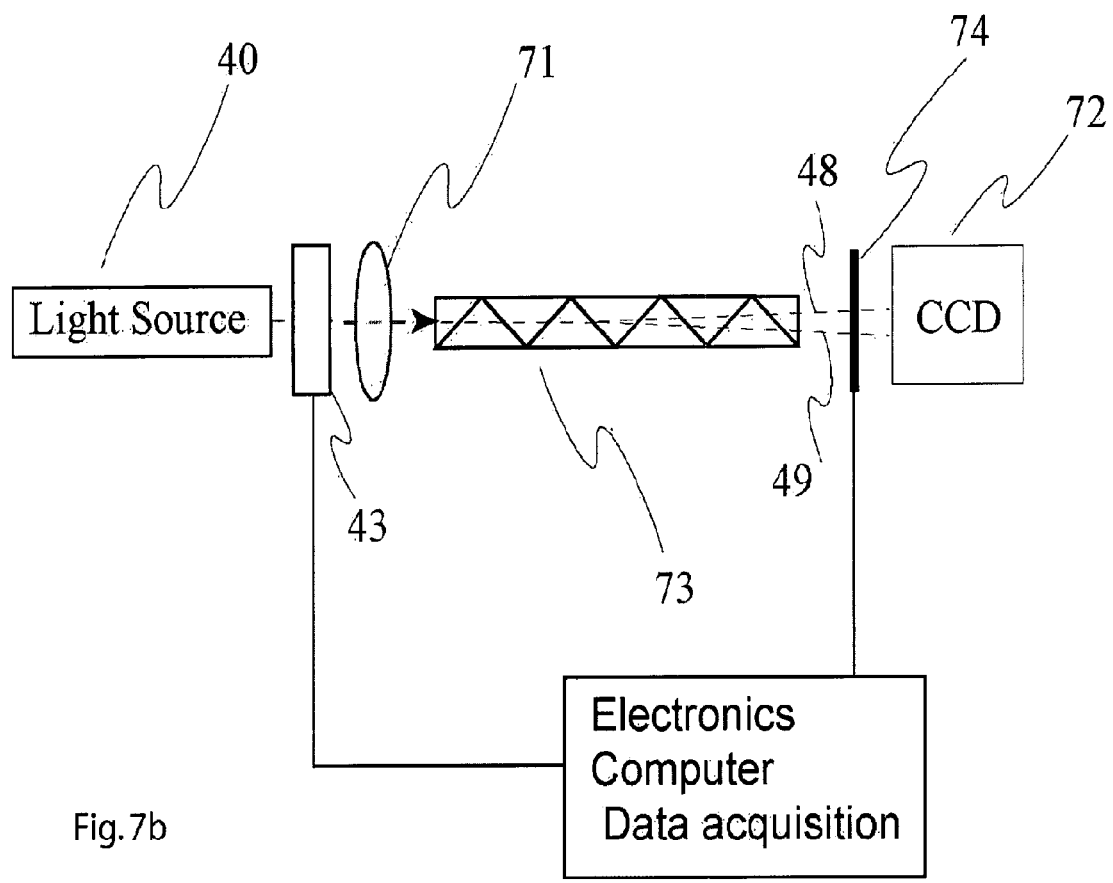
FIG. 7b shows a method to enhance the angular divergence between the left- and the right-circularly polarized beam components using multiple interfaces.

In another embodiment of the present invention, schematically shown in FIGS. 7a and 7b, the separation between the two circularly polarized components is recorded on a CCD 72 camera or other suitable detector. The light from source 40 is typically focused, passed through polarization optics, such as a polarizer and polarization modulator 43 and imaged with lenses or lens-systems and optics 71 through the sample cells 30 in FIG. 7a or similarly combined with the cell arrangement 73 shown in FIG. 7b, onto the CCD camera 72, here a SONY ICX204AL. The sample cells 30 may be replaced by other suitable holders, such as those seen in FIGS. 3a, 8, and 9e, etc. In another embodiment of the present invention, polarization optics 74, such as a polarizer, or a polarizer in combination with a waveplate, can be positioned before the detector. Use of a sample cell geometry 73 that uses multiple interfaces gives rise to multiple differential refraction events between the two circularly polarized components, as has first been suggested by Fresnel (See Fresnel, A. J. in Euvres complètes d' Augustin Fresnel (eds. Sénarmont, H. de, Verdet, É. & Fresnel, L.)), but which is here used in conjunction with phase-sensitive detection. FIG. 7b shows the prismatic cuvettes 73 that are alternately filled with solutions of different optical activities, such as one enantiomer of a chiral liquid and a reference sample with opposite optical activity (possible the opposite enantiomer of said liquid). The modulated beams that have experienced a relative change in their propagation directions (48 and 49) due to the circular birefringence in the optically active sample strike a position sensitive detector at different locations and these may be recorded phase sensitively.

In another embodiment of the invention the cuvette arrangements depicted in FIGS. 4, 6, and 7 may be replaced by other suitable geometries. Examples are shown in FIGS. 8a-c and include a drop 80 of optically active liquid 84 that exhibits circular birefringence and is held on a suitable substrate 81. Linearly polarized light or unpolarized light 10 separates into its two circular polarization components 82 and 83 in the asymmetric refraction geometry. Similarly, the two circularly polarized components incident with the same angle of incidence propagate with different directions according to the principle depicted in FIGS. 2a-b. Another embodiment where the circular birefringence can be measured in accord with the present invention is an asymmetric slab or film 85 shown in FIG. 8b, or a semi-cylindrical capillary 86 with cross-section depicted schematically in FIG. 8c (or otherwise suitably asymmetric capillary).

Figure 1B:
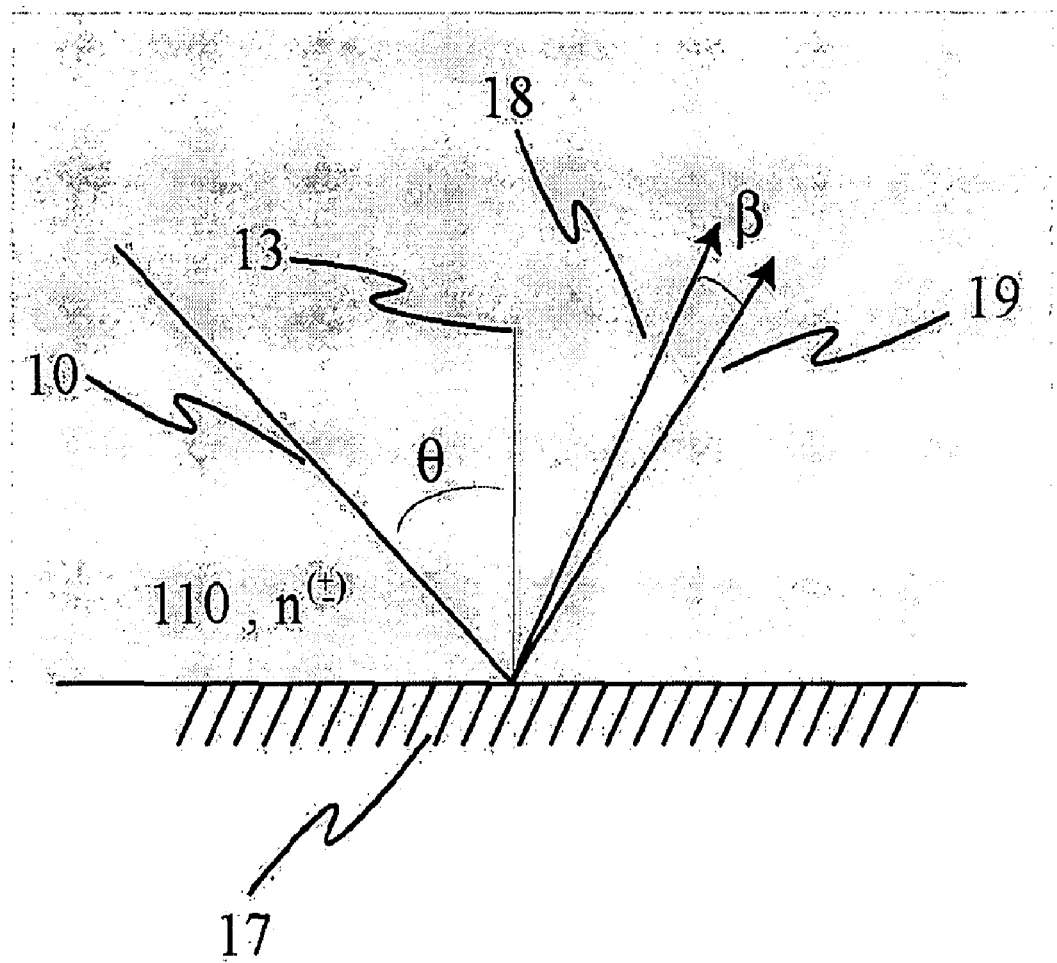
FIG. 1b is a schematic depiction of the reflection of a light beam in an optically active medium at a reflecting surface.
Figure 1C:
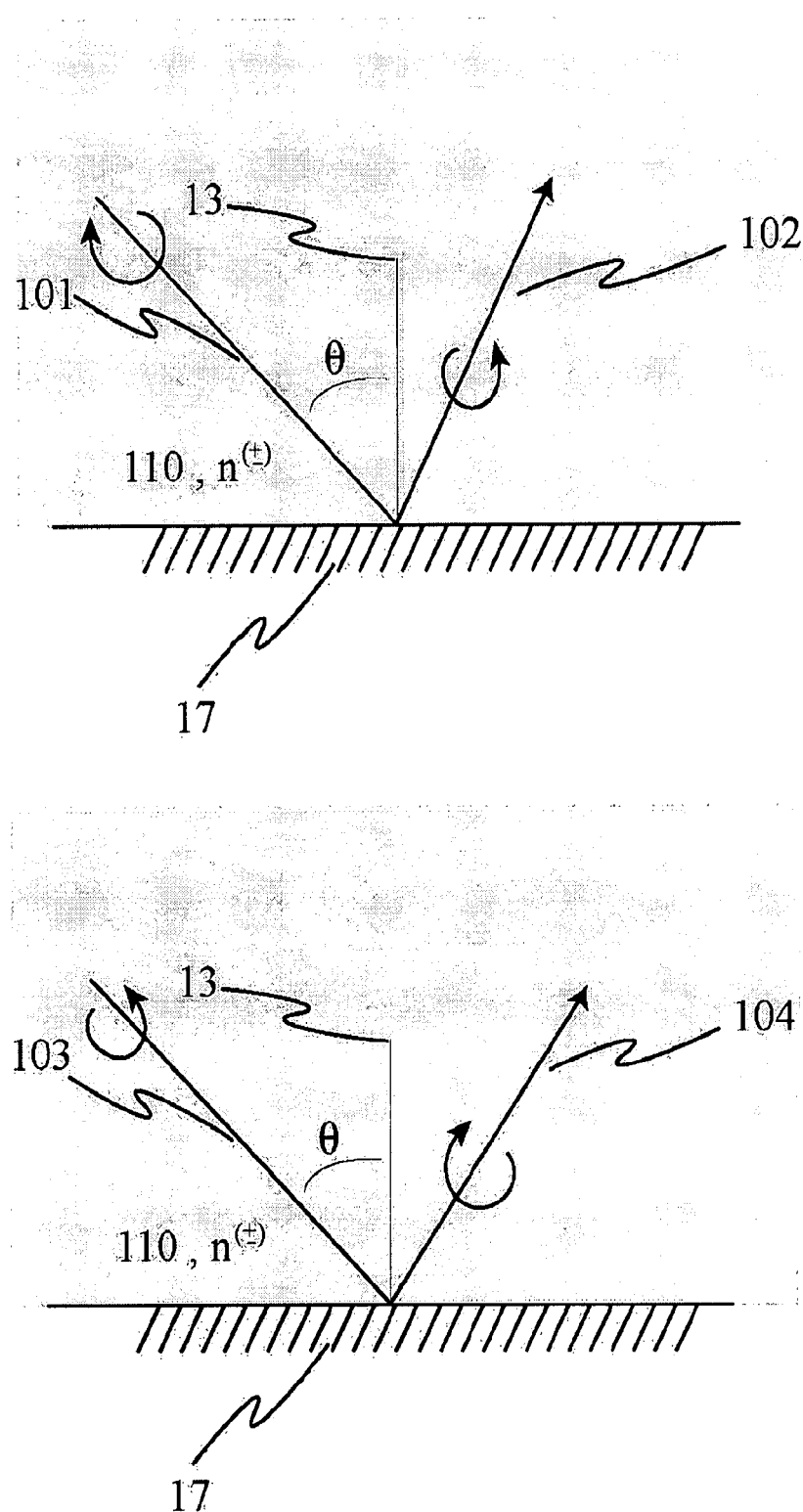
FIG. 1c is a schematic depiction of the reflection of a light beam in an optically active medium at a reflecting surface.

In another embodiment of the present invention the difference in beam direction/position that the circular birefringence gives rise to, is measured in reflection. As shown in FIG. 9a this may be achieved with a drop or hemi-spherical or (or otherwise suitably asymmetric) capillary 95 where the chiral liquid 94 is in contact with a reflecting surface 93 (metal or dielectric) such that the circular polarization components of 10 are reflected with different angles of reflection and propagate in different directions 91 and 92 which may be in detection schemes outlined in the present invention, for example FIGS. 4, 6, 7, or by an intensity based measurement outlined below. FIG. 9b shows that a beam incident normal to one surface of a prismatic sample container 96 with optically active substance 94 may similarly be used. FIG. 9c details how the circular differential reflection in accord with the present invention may be achieved in a thin film or an asymmetric sample that is in contact with an angled reflecting surface 97. Note, that here the effects of diffraction are assumed to be negligible. The incident light of suitable polarization state (possibly modulated) 98 and here schematically shown as a larger beam to emphasize that this embodiment may be particularly suitable for thin sample geometries 902 such as one may find in a microfluidic flow or a flow cell. The principle is the same as that shown in FIGS. 1b and 1c, however, it is here combined with polarization modulation. The reflected light is shown with different directions of propagation 99 and 901 to illustrate that the circular birefringence will cause the reflected beam to exhibit (small) differences in the directions of propagation and that this is a function of the circular birefringence of 94 in accord with the present invention.

Figure 9D:
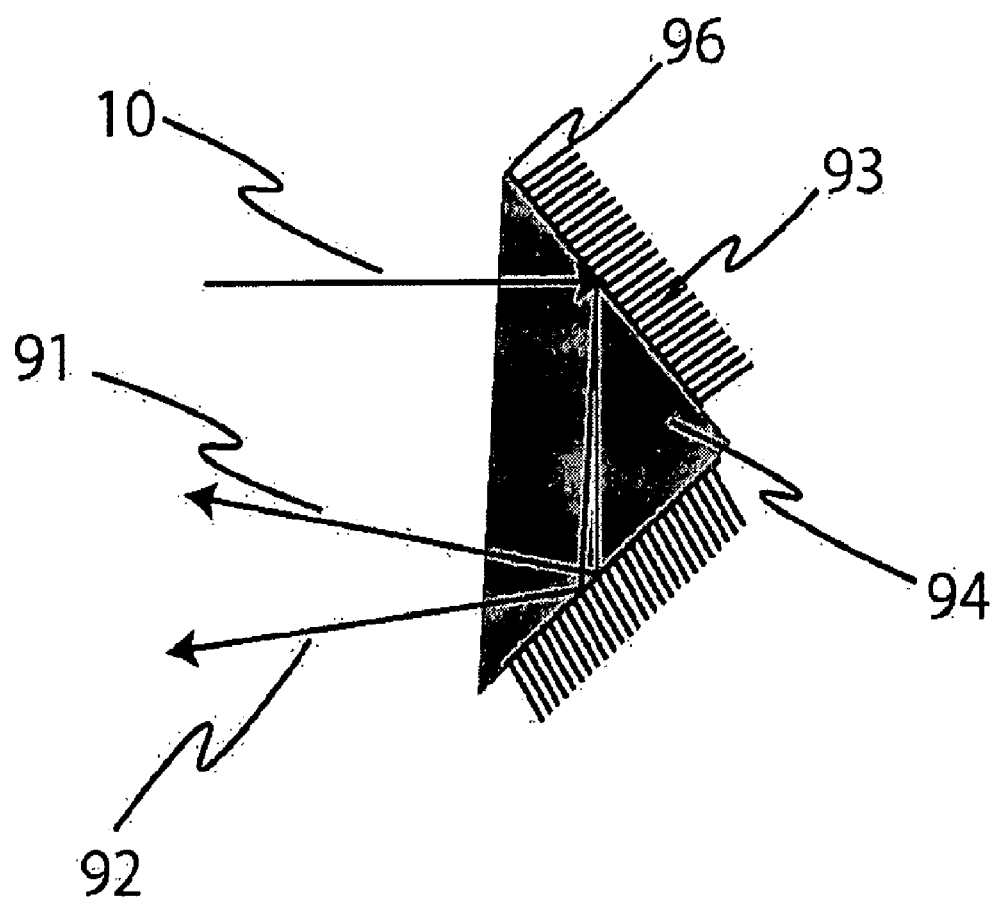
Figure 9E:
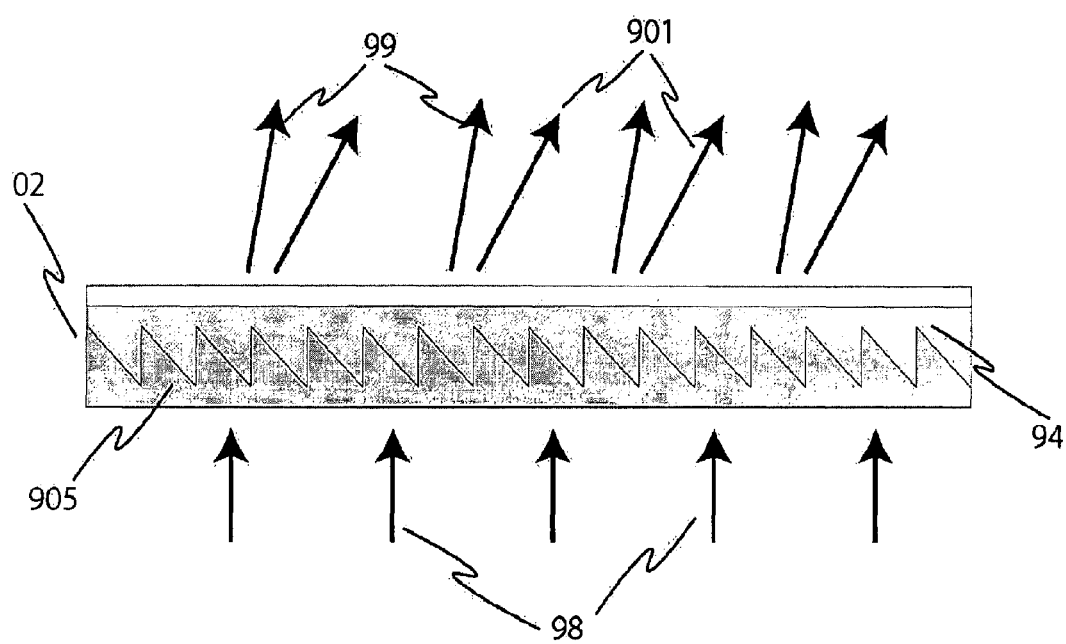
FIG. 9e shows the schematic of a setup used to measure the optical activity of a very small liquid volume. A commercially available Fresnel lens is used to measure the optical activity of a chiral liquid in a small optical path length (on the order of a few hundred microns).

FIG. 9e shows a section of a Fresnel lens 905 that is used to measure the optical activity of a chiral liquid in a small optical path length. Similarly, the saw-tooth shaped surface in FIG. 9c is assumed to allow for the detection of small liquid volumes. The saw-toothed surfaces in FIGS. 9c and 9e may be obtained using grating surfaces, or by microfabrication techniques, such as asymmetric etching, e.g. in the case of FIG. 9c via etching of a single-crystalline Silicon substrate, etc. The refracted and the reflected light in FIGS. 9c and 9e are shown with two different directions of propagation 99 and 901 to illustrate that the circular birefringence will cause the beams to exhibit small differences in the directions of propagation and that this is a function of the circular birefringence of the optically active sample 94 in accord with the present invention.

Figure 10:
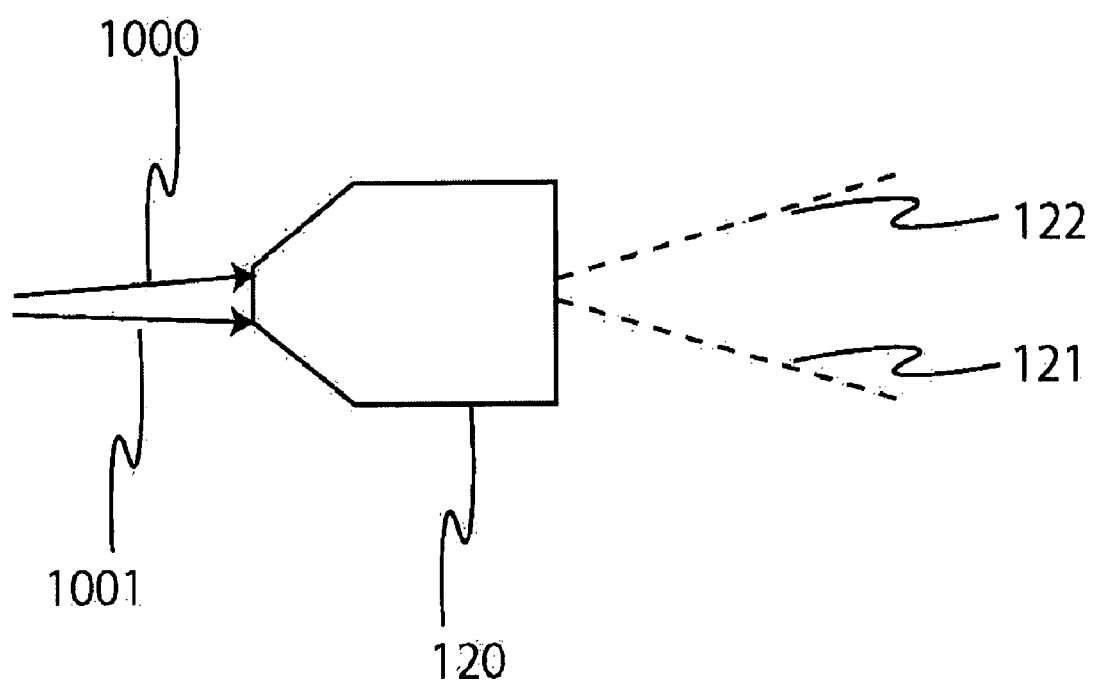
FIG. 10 shows the use of a microscope objective to increase the separation between the two circular polarization components.

The preferred embodiments of the present invention are based on a difference in the propagation directions of two circularly polarized light components with opposite circularity, where the difference in direction is a result of and a measure for circular birefringence, i.e. optical activity. After some distance the two circular components are therefore at different positions in space and this can be detected with a position sensitive detector, as described. FIG. 7c shows that the difference in propagation direction and therefore ultimately the separation between the beams may be increased by multiple refraction events. Similarly, multiple reflection events are possible as shown in FIG. 9d. In addition it is possible to amplify the divergence/separation after the light has interacted with the optically active medium and this is shown in FIG. 10. An imaging system composed of lenses such as a microscope objective 120 increases the separation between the two circular light components 1000 and 1001 to 121 and 122. The net separation between the two light beams results in a larger signal on an appropriate position sensitive detector. The two light components 1000 and 1001 do not have to be present simultaneously. Rather, they are likely to be the result of a direction change of a light beam that is polarization modulated. In this case 1000 and 1001 are present consecutively at the modulation frequency of the polarization modulator, i.e. the light beam moves from one side of the detector to the opposite side at the frequency of the polarization modulator. In addition, it is possible to enhance the position sensitivity by tilting the position sensitive detector such that the light is not normally incident on its surface.

Further, an increase in the separation between two beams 1000 and 1001 that are not parallel beams (have an angular divergence and that do not have to be present simultaneously) may be achieved by multiply-reflecting the beams after the optically active sample and before to the position sensitive detector.

Figure 11A:
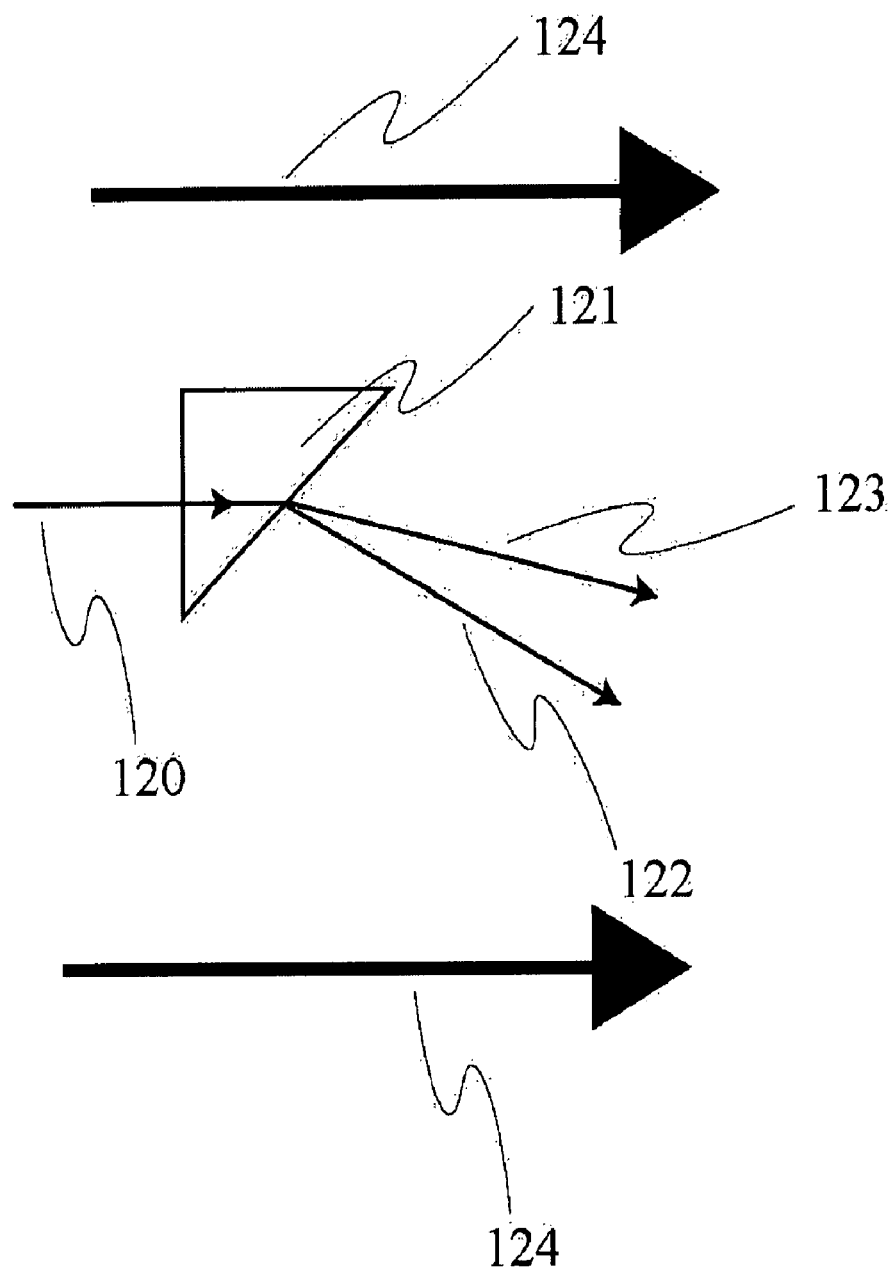
FIG. 11a shows a sample geometry that can be used to determine the angular divergence between the refracting left- and the right-circularly polarized light components induced by a magnetic field.
Figure 11B:
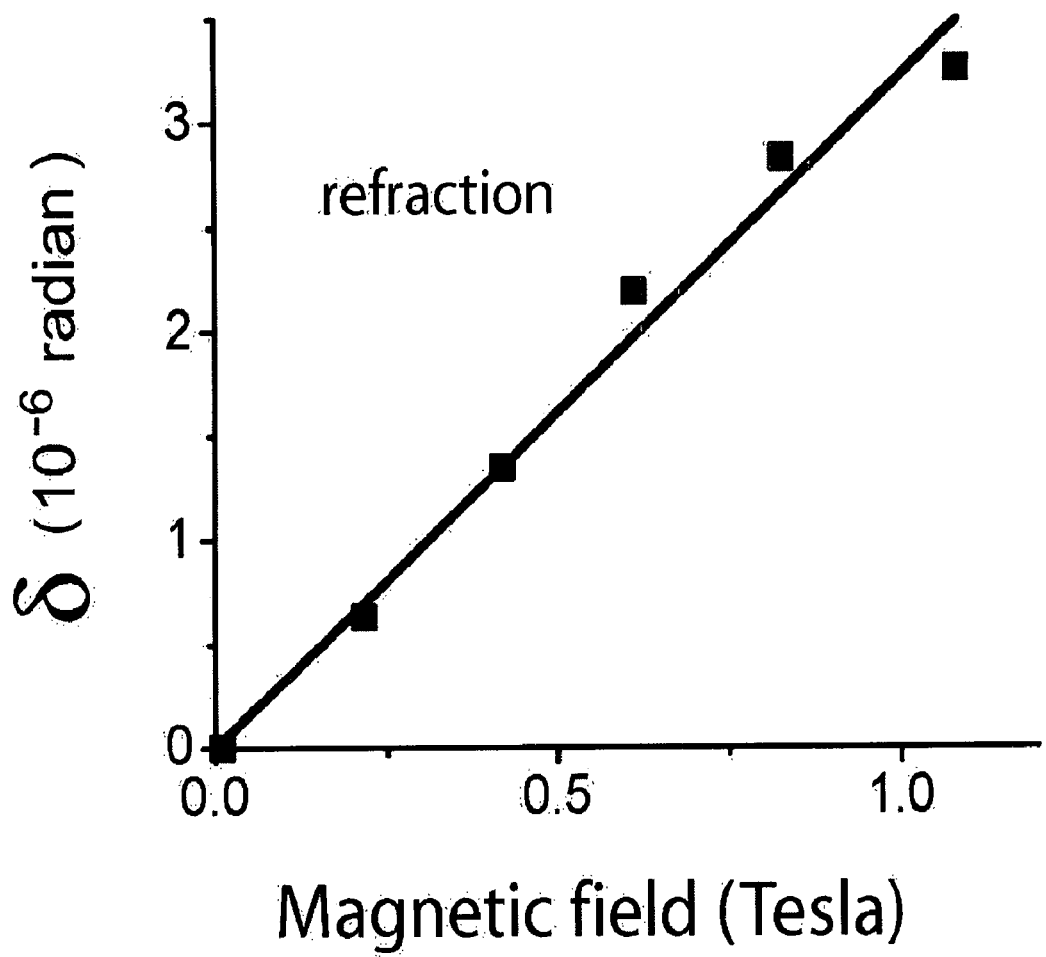
FIG. 11b is a graph of data that shows the difference in the angles of refraction, δ, of the two circularly polarized beams as a function of magnetic field strength. The sample is a transparent glass prism.

FIG. 11a depicts the circular birefringence induced by a magnetic field with direction 124 parallel to the direction of the incident beam 120. The field strength is uniform across the sample. The present invention describes how in suitable geometries the Faraday effect can be observed via the same refraction (and/or reflection and/or diffraction) phenomena that are related to the detection of natural (chiral) circular birefringences (as described in the present invention). The relationship between 11a and 3a is evident. FIG. 11b shows data (angular difference between the left and right circularly polarized light components 122 and 123) that have traversed a prismatic glass 121 (SF11, Schott glass) in the geometry shown in FIG. 11a. The data has been recorded in accord with a preferred embodiment of the present invention. The magnetic field is varied from 0 to just over 1 Tesla in an electromagnet (Walker Scientific HV7) and the light source is a diode pumped solid state laser at 532 nm. The polarization of the beam is modulated by a photoelastic modulator, HINDS Type II FS47, and detected in a scheme similar to that shown in FIG. 4a.

In another embodiment in accord with the present invention the separation between the beams is recorded in an intensity measurement. This may be achieved through the construction of an appropriate optical lever, e.g. see "Some developments and applications of the optical lever", R. V. Jones, Journal of Scientific Instruments, 1961, vol. 38, p. 37-45. The opto-mechanical arrangement at the detector is such that the detection of light intensity (photons) is a measure of the angular separation between the circular polarization components of the beams, or changes in phase as the polarization (circularity) of the incident light is modulated.

In another embodiment in accord with the present invention, the separation between the beams is recorded in an intensity measurement, wherein the beams travel in a geometry such that one of the polarization states is totally internally reflected at an interface and the other state refracts at a grazing angle. This may be achieved through the construction of an appropriately shaped cell (possibly prismatic) that forms and interface between an optically active medium and a reference sample. For certain values of the refractive indices, angle of incidence, etc. the circular components will either undergo total internal reflection or refract at a grazing angle. The intensity of the respective beams may then be measured by suitable detectors (e.g. two balanced photodiodes) and the ratio of the intensities would be a direct measure of the optical activity of the sample.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An apparatus for measuring circular birefringence of an optically active medium which exhibits circular birefringence either due to at least one of chirality or being induced by a magnetic field comprising:
   a container for holding a sample of an optically active medium such that it forms an interface with another medium;
   a light source from which a light beam is incident upon said interface, such that at said interface said light beam refracts, reflects or diffracts;
   means for controlling and manipulating the polarization of said light beam either before or after said sample;
   a detector upon which said reflected, refracted or diffracted light beam is incident which is sensitive to the propagation directions of left and right circularly polarized light components of said refracted, reflected or diffracted light beam and is sensitive to position or positional differences of the light beam(s).

2. An apparatus according to claim 1, wherein said light source comprises at least one of a laser, a lamp, a light emitting diode or any other suitable light source.

3. An apparatus according to claim 1 wherein said detector comprises at least one selected from the group of: a position sensitive detector such as a segmented photodiode, a segmented photomultiplier tube, a position sensitive diode, a CCD camera or other suitable imaging system.

4. An apparatus according to claim 1, wherein said detector is a photodetector and is, in conjunction with polarization and/or focusing optics, is rendered sensitive to position or positional differences of the light beam(s).

5. An apparatus according to claim 1, wherein said detector comprises at least one of a lockin amplifier, a current to voltage converter, a differential amplifier, a data acquisition card and a computer; and wherein said detector measures a measurable parameter of said refracted, reflected or diffracted light beam.

6. An apparatus according to claim 1, wherein said means to control and manipulate the polarization comprises at least one of a photoelastic modulator, an electro-optic modulator, a liquid crystal based modulator and rotating polarization optics.

7. An apparatus according to claim 1, wherein said means to control and manipulate the polarization comprises the light source.

8. An apparatus according to claim 7, wherein said light source comprises a laser that emits light with different polarization components at different frequencies.

9. An apparatus according to claim 8, wherein said laser comprises a Zeeman laser having horizontal and vertical modes, said horizontal and vertical modes being converted to left- and right-circularly polarized light with the use of a waveplate.

10. An apparatus according to claim 1, wherein said sample is in said container such that it gives rise to a refracted or diffracted beam at a suitable interface and where said container is a prismatic cuvette or a cuvette pair such that said beam is also incident on the interface at an angle.

11. An apparatus according to claim 1, wherein said sample is in said container such that it gives rise to a refracted or diffracted beam at a suitable interface and where said container comprises a plurality of prismatic cuvettes such that they form interfaces where said beam is incident on interfaces such that the orientation of the interface changes from one cuvette to the next.

12. An apparatus according to claim 1, wherein said sample is in said container such that it gives rise to a refracted or diffracted beam at a suitable interface and where said container is a surface that supports said sample.

13. An apparatus according to claim 12 wherein said sample is in said container such that it gives rise to a refracted and diffracted beam.

14. An apparatus according to claim 1, wherein said sample is in said container such that it gives rise to a refracted or diffracted beam at a suitable interface and where said container is an asymmetric wedge, or thin film.

15. An apparatus according to claim 1, wherein said sample is in said container such that it gives rise to a refracted or diffracted beam at a suitable interface and where said container confines the liquid in an asymmetric geometry, such as is provided by a semi-cylindrical capillary.

16. An apparatus according to claim 1, wherein said sample is in said container such that it gives rise to a reflected or diffracted beam and wherein said container contains a reflecting surface or suitably reflecting interface that supports said sample.

17. An apparatus according to claim 1, wherein said sample is in said container such that it gives rise to a reflected or diffracted beam and wherein said container is a prismatic cuvette that contains a reflecting surface or that is in contact with a reflecting surface.

18. An apparatus according to claim 1, wherein said sample is in said container such that it gives rise to a reflected beam and wherein said container contains a surface that is formed by a reflection grating in direct contact with the sample, such that light incident normal to the container is also incident normal to the asymmetric surface, and such that the beam is reflected at an angle in the liquid.

19. An apparatus according to claim 1, wherein said sample is in said container such that the beam undergoes multiple reflection, refraction or diffraction events at reflecting, refracting or diffracting surfaces included with the container in direct contact with the liquid sample.

20. An apparatus according to claim 1, wherein said container is part of a flow system such a capillary of geometry such that the optical activity of a flowing sample may be monitored as is for instance required in a detector in chromatography.

21. An apparatus according to claim 1, wherein said sample is in said container such that the beam undergoes a combination of reflection, refraction or diffraction events at suitable surfaces such that the combination of these events permits detection, measurement or monitoring of optical activities.

22. An apparatus according to claim 1, wherein said sample container or optical components are microfabricated or part of a microfluidic device.

23. An apparatus for measuring a difference in the propagation directions between left- and right-circularly polarized light beams or a difference in propagation directions of left- and right-circularly polarized light components that have refracted, reflected or diffracted at an interface formed by a sample and another medium, where one or more interfaces give rise to differences in the angles of refraction, reflection or diffraction of the left- and right-circularly polarized light beams, comprising:
   one or more light beams from one or more light sources emitting light at one or more frequencies;
   a means for directing at least portions thereof onto a sample in a suitable container;
   a means to set and/or change a polarization state of said light beam either before it is incident upon an interface where refraction, reflection or diffraction of interest occurs, or after said interface but before the light beam is detected;

a means for directing the light beam after it has refracted, reflected or diffracted onto a detector that provides a signal which is proportional to a relative position of said light beam as a function of the polarization state of the light beam;

a means for correcting for changes in said light beams' position on the detector that are unrelated to circular birefringence by means of signal averaging, a reference measurement, a detector monitoring beam, polarization or refractive index fluctuations.

24. An apparatus according to claim 23 further comprising:

multiple interfaces or a beam geometry that allows for multiple refraction, reflection or diffraction events at one or more interfaces using suitable optics, where the interfaces are in contact with the sample, such that the angular divergence upon refraction, reflection or diffraction are due to circular birefringence, between the left- and right circularly polarized light components is increased after each refraction, reflection or diffraction event or such that the multitude of interfaces, configured such that the angular divergence in an optically active sample is as high as required or possible.

25. An apparatus according to claim 23 further comprising:

means for modulating the light that is incident upon said interface of interest between left- and right-circularly polarized light states;

means for determining and recording the positions of said light as a function of its modulated polarization state and thereby a means to determine the angular separation of the light beams and hence deduce the circular birefringence of the sample of interest, and deduce the optical rotation per unit length of said optically active sample.

26. An apparatus according to claim 23 further comprising:

a means for selecting polarization components after they have interacted with the sample a means for determining and recording the intensity or positions of said light as a function of the selected polarization state and thereby a means to determine the difference in the angles of refraction, reflection or diffraction of the circular polarization components of the light.

27. An apparatus according to claim 23 further comprising a means to determine the position of said light phase-sensitively or with respect to a reference compound.

28. An apparatus according to claim 23 further comprising a means to determine the position of said light beam as the sample is changed with a pump or through a flow in a flow-cell, a microfluidic device or a capillary and thereby determining the optical activity, circular birefringence, enantiomeric excess, optical purity, optical rotation, chemical composition or refractive index of said sample or a number of said samples.

29. An apparatus according to claim 23 further comprising a means to determine the position of said light as a part of the sample undergoes a chemical reaction and at least one of the optical activity, circular birefringence, enantiomeric excess, optical rotation, chemical composition and refractive index of said sample is monitored.

30. An apparatus according to claim 23, where the angle of incidence of the beam incident upon an interface formed by the sample and another medium can be varied and where it can be chosen such that it gives rise to a difference in the beam propagation directions of the left- and right-circularly polarized beam(s) upon refraction, reflection and/or diffraction, at one or more interfaces, this may include total internal reflection of one or more polarization components of the light.

31. A method for increasing the angular divergence and/or separation between the circularly differentially refracted and/or reflected and/or diffracted beams after they have interacted with the sample of interest, comprising:

increasing the distance between the detector and the sample such that the light is incident upon the position sensitive detector with a non-zero angle of incidence.

32. The method of claim 31 further comprising an imaging system, such as a microscope objective, such that the separation or angular divergence between the beam(s) is increased before it is incident upon a suitable detector.

* * * * *